United States Patent
Shalwitz

(10) Patent No.: US 12,370,209 B2
(45) Date of Patent: *Jul. 29, 2025

(54) METHODS FOR THE USE OF 5'-ADENOSINE DIPHOSPHATE RIBOSE (ADPR)

(71) Applicant: Invirsa, Inc., Columbus, OH (US)

(72) Inventor: Robert Shalwitz, Bexley, OH (US)

(73) Assignee: Invirsa, Inc., Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/503,967

(22) Filed: Nov. 7, 2023

(65) Prior Publication Data

US 2024/0091249 A1 Mar. 21, 2024

Related U.S. Application Data

(62) Division of application No. 17/392,578, filed on Aug. 3, 2021, now Pat. No. 11,857,561, which is a division of application No. 15/999,269, filed as application No. PCT/US2017/018253 on Feb. 17, 2017, now Pat. No. 11,110,112.

(60) Provisional application No. 62/428,721, filed on Dec. 1, 2016, provisional application No. 62/296,665, filed on Feb. 18, 2016.

(51) Int. Cl.
| | | |
|---|---|---|
| *A61K 31/7076* | (2006.01) | |
| *A61K 9/00* | (2006.01) | |
| *A61K 31/522* | (2006.01) | |
| *A61K 31/675* | (2006.01) | |
| *A61K 33/24* | (2019.01) | |
| *A61K 33/30* | (2006.01) | |
| *A61K 33/34* | (2006.01) | |
| *A61P 27/02* | (2006.01) | |
| *A61P 35/00* | (2006.01) | |
| *C07H 19/207* | (2006.01) | |

(52) U.S. Cl.
CPC ........ *A61K 31/7076* (2013.01); *A61K 9/0014* (2013.01); *A61K 31/522* (2013.01); *A61K 31/675* (2013.01); *A61K 33/24* (2013.01); *A61K 33/30* (2013.01); *A61K 33/34* (2013.01); *A61P 27/02* (2018.01); *A61P 35/00* (2018.01); *C07H 19/207* (2013.01)

(58) Field of Classification Search
CPC .... A61K 31/7076; A61K 9/00; A61K 31/522; A61K 31/675; A61K 33/30; A61K 33/24; A61K 33/34; A61P 27/02; A61P 35/00; C07H 19/207

See application file for complete search history.

(56) References Cited

U.S. PATENT DOCUMENTS

| | | |
|---|---|---|
| 6,331,529 B1 | 12/2001 | Yerxa et al. |
| 6,436,910 B1 | 8/2002 | Yerxa et al. |
| 6,528,042 B1 | 3/2003 | Brown et al. |
| 6,989,260 B2 | 1/2006 | Christenson et al. |
| 7,115,585 B2 | 10/2006 | Yerxa et al. |
| 10,946,034 B2 | 3/2021 | Shalwitz |
| 11,110,112 B2 | 9/2021 | Shalwitz |
| 11,793,826 B2 | 10/2023 | Shalwitz et al. |
| 11,857,561 B2 | 1/2024 | Shalwitz |
| 12,233,083 B2 | 2/2025 | Shalwitz et al. |
| 2002/0052338 A1 | 5/2002 | Yerxa et al. |
| 2003/0008834 A1 | 1/2003 | Yerxa et al. |
| 2003/0236217 A1 | 12/2003 | Shalwitz et al. |
| 2005/0009777 A1 | 1/2005 | Mack et al. |
| 2005/0276762 A1 | 12/2005 | Das et al. |
| 2007/0212395 A1 | 9/2007 | Donello et al. |
| 2008/0081796 A1 | 4/2008 | Shalwitz et al. |
| 2008/0305994 A1 | 12/2008 | Zhang et al. |
| 2011/0217262 A1 | 9/2011 | Kornfield et al. |
| 2013/0116284 A1 | 5/2013 | Salzman |
| 2015/0038473 A1 | 2/2015 | Stein et al. |
| 2019/0298752 A1 | 10/2019 | Shalwitz et al. |
| 2020/0330498 A1 | 10/2020 | Shalwitz |
| 2021/0161936 A1 | 6/2021 | Shalwitz et al. |
| 2022/0054522 A1 | 2/2022 | Shalwitz |
| 2023/0414647 A1 | 12/2023 | Shalwitz et al. |

FOREIGN PATENT DOCUMENTS

| | | |
|---|---|---|
| EP | 0701562 B1 | 6/1997 |
| EP | 1948215 B1 | 1/2012 |
| EP | 2647382 A1 | 10/2013 |
| JP | H 07247210 | 9/1995 |
| WO | WO 1999/12951 | 3/1999 |
| WO | WO 2003/072067 A1 | 9/2003 |
| WO | WO 2003/099297 A1 | 12/2003 |
| WO | WO 2005/123030 A1 | 12/2005 |
| WO | WO 2006/127987 A2 | 11/2006 |
| WO | WO 2007/054814 A1 | 5/2007 |
| WO | WO 2015/073319 A1 | 5/2015 |

(Continued)

OTHER PUBLICATIONS

Medical News Today by Cattamanchi (2019).*
Aleo et al., 1996, "Enzymatic activites affecting exogenous nicotinamide adenine dinucleotide in human skin fibroblasts", J Cell Physiol, 167:173-176.
Braun, 2014, "A novel disease connection for TRPM2 channels", Channels, 8(6):475-476.
Clement et al., 2011, "Clinical and antiviral efficacy of an ophthalmic formulation of dexamethasone povidone-iodone in a rabbit model of adenoviral keratoconjunctivitis", Investigative Ophthalmology & Visual Science, 52(1):339-344.
Gil-Fernandez et al., 1987, "Antiviral activity of uridine 5'-diphosphate glucose analogues against some enveloped viruses in cell culture", Antiviral Research, 8:299-310.
Hottiger, 2015, SnapShot: ADP-ribosy lation signaling, Molecular Cell, 58:1134.

(Continued)

*Primary Examiner* — Shirley V Gembeh

(74) *Attorney, Agent, or Firm* — Jones Day

(57) ABSTRACT

The present invention is directed to methods for the use of 5'-adenosine diphosphate ribose (ADPR), and compositions thereof, for treating, managing, or preventing adenovirus-related diseases or conditions, eye disorders, cancer, or diseases or conditions caused by infection, inflammation, or physical, chemical, thermal, or radiation injuries.

20 Claims, 18 Drawing Sheets

(56) References Cited

FOREIGN PATENT DOCUMENTS

| WO | WO 2017/143113 A1 | 8/2017 |
|---|---|---|
| WO | WO 2019/191026 A2 | 10/2019 |

OTHER PUBLICATIONS

Houlsby et al., 1986, "Antimicrobial activity of borate-buffered solutions", Antimicrobial Agents and Chemotherapy, 29(5):803-806.

Huang et al., 2014, Extracellular ADP-ribose induces [Ca2+] pathway in pulmonary artery smooth muscle cells, FASEB J, 28(1):Suppl 1175.4.

Im and Hoopes, 1989, "Improved skin flap survival with nicotinic acid and nicotinamide in rats", J Surg Res, 47:453-455.

International Search Report dated May 29, 2017 of International Application No. PCT/US2017/018253.

Johns et al., 2007, "Cytoprotective agent in lactobacillus bulgaricus extracts", Current Microbiology, 54(2):131-135.

Lin et al., 2012, "Niacinamide mitigated the acute lung injury induced by phorbol myristate acetate in isolated rat's lungs", J Biomed Sci, 19(27):1-13.

Lion, 2014, "Adenovirus infections in immunocompetent and immunocompromised patients", Clin Microbiol Rev, 27(3):441-462.

Martínez-Aguado et al., 2015, "Antiadenovirus drug discovery: potential targets and evaluation methodologies", Drug Discovery Today, 20(10):1235-1242.

Neurath et al., 1970, "Disruption of adenovirus type 7 by lithium iodide resulting in the release of viral deoxyribonucleic acid", J Virol, 5(2):173-178.

Paoletti et al., 2012, "Multifaceted roles of purinergic receptors in viral infection", Microbes and Infection, 14(14):1278-1283.

Van Groeningen et al., 1992, "Modulation of fluorouracil toxicity with uridine", Seminars in Oncology, 19(2)Suppl 3:148-154.

Virág and Szabó, 2002, "The therapeutic potential of poly (ADP-ribose) polymerase inhibitors", Phamacol Rev, 54(3):375-429.

Wright et al., 2016, "ADP-ribose-derived nuclear ATP synthesis by NUDIX5 is required for chromatin remodeling", Science, 352(6290):1221-1225.

Written Opinion dated May 29, 2017 of International Application No. PCT/US2017/018253.

Budayeva et al., 2015, "The intricate roles of mammalian sirtuins in defense against viral pathogens," J. Virol., 90(1):5-8.

Chen et al., 2013, "Pax6 Downregulation Mediates Abnormal Lineage Commitment of the Ocular Surface Epithelium in Aqueous-Deficient Dry Eye Disease," PLoS One, 8(10):e77286.

Koyuncu et al., 2014, "Sirtuins are Evolutionarily Conserved Viral Restriction Factors," Mbio, 5(6):e02249-14.

Li et al., 2008, "Down-regulation of Pax6 is associated with abnormal differentiation of corneal epithelial cells in severe ocular surface diseases, " J. Pathol., 214(1):114-122.

McNamara et al., 2014, "Establishing PAX6 as a Biomarker to Detect Early Loss of Ocular Phenotype in Human Patients With Sjogren's Syndrome," Invest. Ophthalmol. Vis. Sci., 55:7079-7084.

Pan et al., 2011, "Structure and Biochemical Functions of SIRT6," J. Biol. Chem., 286(16):14575-14587.

Khan et al., 2006, "Use of Substrate Analogs and Mutagenesis to Study Substrate Binding and Catalysis in the Sir2 Family of NAD-dependent Protein Deacetylases," J. Biol. Chem., 281(17): 11702-11711.

Priest et al., 2010, "Deconstructing nucleotide binding activity of the Mdm2 RING domain," Nucleic Acids Res., 38(21):7587-7598.

Poyurovsky et al., 2003, "Nucleotide Binding by the MDM2 Ring Domain Facilitates Arf-Independent MDM2 Nucleolar Localization," Mol. Cell, 12(4):875-887.

Zhang et al., 2014, "Aberrant activation of p53 due to loss of MDM2 or MDMX causes early lens dysmorphogenesis," Dev. Biol., 396(1):19-30.

Thirumurthi et al., 2014, "MDM2-mediated degradation of SIRT6 phosphorylated by AKT1 promotes tumorigenesis and trastuzumab resistance in breast cancer," Sci. Signal, 7(336):ra71.

Bawage et al., 2013, "Recent Advances in Diagnosis, Prevention, and Treatment of Human Respiratory Synctial Virus", Advances in Virology, 203:1-26.

Blumberg et al., 1989, "Herpes Zoster," Clinics in Dermatology, 7(1):37-48.

Nikkels et al., 1994, "Recognition and Treatment of Shingles," Drugs, 48(4):529-548.

Haile et al., 2011, "The Activity of an Ancient Atypical Protein Kinase is Stimulated by ADP-Ribose in vitro," Archives of Biochemistry & Biophysics, 511:56-63.

Malanga et al., 1998, "Polu(ADP-Ribose) Binds to Specific Domains of p53 and Alters its DNA Binding Functions," Journal of Biological Chemistry, 273(19):11839-11843.

International Search Report dated Oct. 28, 2019 of International Application No. PCT/US2019/023977.

Written Opinion dated Oct. 28, 2019 of International Application No. PCT/US2019/023977.

Office Action dated Apr. 16, 2020 in U.S. Appl. No. 16/364,760.

Office Action dated Sep. 28, 2020 in U.S. Appl. No. 16/364,760.

Restriction Requirement dated Jan. 19, 2021 in U.S. Appl. No. 15/999,269 (9 pages).

Notice of Allowance dated Dec. 30, 2020 in U.S. Appl. No. 16/364,760.

Aloni-Grinstein et al., 2018, "p53 and the Viral Connection: Back into the Future," Cancers (Basel), 10(6):178.

Tendler et al., 2020, "Features of p53 protein distribution in the corneal epithelium and corneal tear film," Sci. Rep., 10(1):10051; pp. 1-7.

Zykova et al., 2018, "Targeting PRPK Function Blocks Colon Cancer Metastasis," Mol. Cancer Ther., 17(5):1101-1113.

Albeniz et al., 2004, "NAD Glycohydrolase Activities and ADP-Ribose Uptake in Erythrocytes From Normal Subjects and Cancer Patients," Bioscience Reports, 24(1):41-53.

Kim et al., 1993, "Function of NAD glycohydrolase in ADP-ribose uptake from NAD by human erythrocytes," Biochim. Biophys. Acta., 1178(2):121-126.

Office Action dated Apr. 8, 2021 in U.S. Appl. No. 15/999,269 (15 pages).

Notice of Allowance dated Jun. 23, 2021 in U.S. Appl. No. 15/999,269 (9 pages).

Banker et al., Modern Pharmaceutics, 3rd Ed., Marcel Dekker, New York, 1996, pp. 451 and 596.

Wolff, M. E., Burger's Medicinal Chemistry and Drug Discovery, 5th Ed., vol. I, John Wiley & Sons, 1995, pp. 975-977.

Vippagunta et al., 2001, "Crystalline Solids," Advanced Drug Delivery Reviews, 48(2001):3-26.

Tepedelen et al., 2016, "Boric acid reduces the formation of DNA double strand breaks and accelerates wound healing process", Biol Trace Elem Res, 174:309-318.

Kim et al., 2003, "Esterification of borate with NAD$^+$ and NADH as studied by electrospray ionization mass spectrometry and 11B Nmr spectroscopy", Journal of Mass Spectrometry, 38:632-640.

Kim et al., 2006, "Boric acid inhibits adenosine diphosphate-ribosyl", Journal of Chromatography A, 1115:246-252.

Falsey et al., 2005, "Respiratory Syncytial Virus Infection in Elderly and High-Risk Adults," The New England Journal of Medicine, 352(17):1749-1759.

Feldman et al., 2013, "Activation of the Protein Deacetylase SIRT6 by Long-chain Fatty Acids and Widespread Deacy lation by Mammalian Sirtuins," Journal of Biological Chemistry, 288(43):31350-31356.

Feldman et al., 2015, "Toward Primary Prevention of Asthma. Reviewing the Evidence for Early-Life Respiratory Viral Infections as Modifiable Risk Factors to Prevent Childhood Asthma," American Journal of Respiratory and Critical Care Medicine, 191(1):34-44.

Griffiths et al., 2017, "Respiratory Syncytial Virus: Infection, Detection, and New Options for Prevention and Treatment," Clinical Microbiology Reviews, 30(1):277-319.

(56) References Cited

OTHER PUBLICATIONS

Hall et al., 2009, "The Burden of Respiratory Syncytial Virus Infection in Young Children," The New England Journal of Medicine, 360(6):588-598.
Heiner et al., 2006, "Endogenous ADP-ribose enables calcium-regulated cation currents through TRPM2 channels in neutrophil granulocytes," Biochemical Journal, 398(2):225-232.
Iwane et al., 2013, "Importance of global surveillance for respiratory syncytial virus," Journal of Infectious Diseases, 208(Suppl. 3):2-3.
Jiang et al., 2013, "SIRT6 regulates TNF—a secretion through hydrolysis of long-chain fatty acyl lysine," Nature, 496:110-113 (6 pages, including supplementary information).
Kugel et al., 2014, "Chromatin and beyond: The multitasking roles for SIRT6," Trends in Biochemical Sciences, 39(2):72-81.
Madsen et al., 2016, "Investigating the Sensitivity of NAD+-dependent Sirtuin Deacylation Activities to NADH," Journal of Biological Chemistry, 291(13):7128-7141.
McCormick and Mocarski Jr., 2007, "Viral modulation of the host response to infection," Chapter 21 in Human Herpesviruses: Biology, Therapy, and Immunoprophylaxis, Arvin, A. et al. Eds., Cambridge: Cambridge University Press (13 pages).
Michishita et al., 2008, "SIRT6 is a histone H3 lysine 9 deacetylase that modulates telomeric chromatin," Nature, 452(7186):492-496.
Rahnasto-Rilla et al., 2016, "Sirtuin 6 (SIRT6) Activity Assays," Methods in Molecular Biology, 1436:259-269 (author manuscript; 11 pages).
Rose et al., 2018, "Respiratory Syncytial Virus Seasonality—United States, 2014-2017," Centers for Disease Control and Prevention: Morbidity and Mortality Weekly Report (MMWR), 67(2):71-76.
Tasselli et al., 2017, "SIRT6: Novel Mechanisms and Links to Aging and Disease," Trends in Endocrinology and Metabolism, 28(3):168-185.
Office Action dated Aug. 18, 2022 in U.S. Appl. No. 17/171,548 (12 pages).
Qi et al., 2022, "The ADP-Ribose Hydrolase NUDT5 is Important for DNA Repair," Cell Reports, 41(12):111866 (13 pages).
Sears, C. R., 2019, "DNA Repair as an Emerging Target for COPD-Lung Cancer Overlap," Respir. Investig., 57(2):111-121.
Sears, C. R., 2018, "Xeroderma Pigmentosum Group C Deficiency Alters Cigarette Smoke DNA Damage Cell Fate and Accelerates Emphysema Development," Am. J. Respir. Cell Mol. Biol., 58(3):402-411.
Lerche, et al., 2012, "Topical Nutlin-3a Does Not Decrease Photocarcinogenesis Induced by Simulated Solar Radiation in Hairless Mice," Photodermatology, Photoimunology & Photomedicine, 28:207-212.
Office Action dated Mar. 14, 2023 in U.S. Appl. No. 17/171,548.
Benjamin et al., 2007, "P53 and the pathogenesis of skin cancer," Toxicology and Applied Pharmacology, vol. 224, pp. 241-248.
Nefedova et al., 2017, "In vitro study of anti-influenza activity of para-aminobenzoic acid and prospects of nasal drug development on its base," Annals of Mechnikov's Institute, N2:20-22.
Notice of Allowance dated Jan. 6, 2023 in U.S. Appl. No. 17/171,548.
Office Action dated May 4, 2023 in U.S. Appl. No. 17/392,578.
Notice of Allowance dated Aug. 9, 2023 in U.S. Appl. No. 17/392,578.
Notice of Allowance dated Aug. 29, 2023 in U.S. Appl. No. 17/171,548.
Choi et al., 2008, "Prediction of cis-regulatory elements controlling genes differentially expressed by retinal and choroidal vascular endothelial cells," J. Ocul Biol Dis Inform, 1:37-45.
Fan et al., 2018, "Inhibition of Noncanonical Murine Double Minute 2 Homolog Abrogates Ocular Inflammation through NF-κB Suppression," The American Journal of Pathology, 188(9):2087-2096.
Kria et al., 2005, "Immunohistochemical study of vascular endothelial growth factor (VEGF), tumor suppressor protein (p53) and intercellular adhesion molecule (ICAM-1) in the conjuctiva of diabetic patients," Journal of Molecular Histology, 36:381-390.
Moysidis et al., 2012, "Mechanisms of Inflammation in Proliferative Vitreoretinopathy: From Bench to Bedside," Mediators of Inflammation (Hindawi Publishing Corporation) vol. 2012, Article ID 815937 (11 pages).
Lei et al., 2012, "A Novel Function of p53: A Gatekeeper of Retinal Detachment," The American Journal of Pathology, 181(3):866-874.
Wiley et al., 2011, "The tumor suppressor gene Trp53 protects the mouse lens against posterior subcapsular cataracts and the BMP receptor Acvr1 acts as a tumor suppressor in the lens," Disease Models & Mechanisms, 4:484-495.
Chavala et al., 2013, "Retinal angiogenesis suppression through small molecule activation of p53," The Journal of Clinical Investigation, 123(10):4170-4181.
Wang et al., 2013, "Overexpression of SIRT1 Promotes High Glucose-Attenuated Corneal Epithelial Wound Healing via p53 Regulation of the IGFBP3/IGF-1R/AKT Pathway," IOVS, 54(5):3806-3814.
Shalwitz et al., 2024, "Treatment of Sulfur Mustard Corneal Injury by Augmenting the DNA Damage Response (DDR): A Novel Approach," J Pharmacol Exp Ther, 388:526-535.
U.S. Appl. No. 19/029,481, filed Jan. 17, 2025, Shalwitz et al.
Cattamanchi, A, 2019, "What to know about an exacerbation of COPD," Medical News Today, Sep. 30, 2019 (8 pages).
Notice of Allowance dated Dec. 4, 2024 in U.S. Appl. No. 18/244,693.

\* cited by examiner

E

F

G

G

H

I

J

METHODS FOR THE USE OF 5'-ADENOSINE DIPHOSPHATE RIBOSE (ADPR)

CROSS-REFERENCES TO RELATED APPLICATIONS

This application is a divisional application of U.S. patent application Ser. No. 17/392,578, filed Aug. 3, 2021, currently allowed, which is a divisional application of U.S. patent application Ser. No. 15/999,269, filed Aug. 17, 2018, now U.S. Pat. No. 11,110,112, issued Sep. 7, 2021, which is a national stage of International Patent Application No. PCT/US2017/018253, filed Feb. 17, 2017, which claims the benefit of U.S. Provisional Patent Application No. 62/296,665, filed Feb. 18, 2016, and U.S. Provisional Patent Application No. 62/428,721, filed Dec. 1, 2016, each of which is incorporated herein by reference in its entirety.

1 FIELD OF THE INVENTION

The present invention is directed to methods for the use of 5'-adenosine diphosphate ribose (ADPR), and compositions thereof, for treating, managing, or preventing adenovirus-related diseases or conditions, eye disorders, cancer, or diseases or conditions caused by infection, inflammation, or physical, chemical, thermal, or radiation injuries.

2 BACKGROUND OF THE INVENTION

Human adenoviruses have been well established as infectious agents in both immunocompetent as well as immunocompromised individuals. Human adenovirus infections have been shown to be the cause of high morbidity and mortality in immunocompromised individuals. Despite their life-threatening nature, there are currently no approved antiviral therapies for human adenovirus infections (see Lion, 2014, "Adenovirus Infections in Immunocompetent and Immunocompromised Patients," Clin. Microbiol. Rev., 27(3):441-462; Martinez-Aguado et al., 2015 "Antiadenovirus Drug Discovery: Potential Targets and Evaluation Methodologies," Drug Discov. Today, 20(10):1235-1242. Broadly acting antiviral drugs such as cidofovir, ribavirin, and ganciclovir are some of the suboptimal therapeutic options for the treatment of adenovirus infections; however, the results have been variable. Cidofovir has been shown to exhibit antiviral activity against all human adenovirus species; however, it is associated with low bioavailability, poor correlation of pharmacologic effects with the prescribed dose, and dose-limiting nephrotoxicity. Ribavirin has variable activity against different human adenovirus types, displaying maximum activity against subtype C; however, the evidence for therapeutic efficacy of ribavirin in vivo remains controversial in light of the low plasma concentrations achieved with this compound. The use of ganciclovir is also suggested to treat human adenovirus infections, but its activity against this virus is relatively poor.

5'-adenosine diphosphate ribose (ADPR) is a naturally occurring small molecule, which is also available commercially. ADPR has been demonstrated to possess anti-cytotoxic properties, through its identification as a significant contributor to the anti-cytotoxic activity of *Lactobacillus bulgaricus* extracts; in vitro, ADPR levels as low as 5 mg/L exhibited a measurable inhibition of tumor necrosis factor alpha (TNF-α) mediated cytotoxicity (see Johns et al., 2007, "Cytoprotective Agent in *Lactobacillus bulgaricus* Extracts," Current Microbiology, 54(2):131-135). The use of ADPR has also been implicated for preventing, retarding or treating the harmful effects of solar radiation on the skin (see WO 2005/123030 A1). ADPR has also been shown to effectively alleviate mucositis in susceptible individuals, especially when administered prior to, during, or after treatments commonly associated with the development of mucositis such as certain chemotherapies, radiation therapies, or combinations thereof (see WO 03/099297 A1).

It has been found that ADPR and its compositions provided herein can be used effectively for treating, managing, or preventing adenovirus-related diseases or conditions, eye disorders, cancer, or diseases or conditions caused by infection, inflammation, or physical, chemical, thermal, or radiation injuries.

3 SUMMARY OF THE INVENTION

Provided herein are methods for treating, managing, or preventing adenovirus-related diseases or conditions, eye disorders, cancer, or diseases or conditions caused by infection, inflammation, or physical, chemical, thermal, or radiation injuries, such as those provided herein, comprising administering 5'-adenosine diphosphate ribose (ADPR) or a pharmaceutically acceptable salt, solvate, hydrate, tautomer, stereoisomer, isotopologue, pro-drug, or polymorph thereof, or a pharmaceutical composition thereof, to a patient having or at risk of developing an adenovirus-related disease or condition, an eye disorder, cancer, or a disease or condition caused by infection, inflammation, or physical, chemical, thermal, or radiation injuries.

In a specific embodiment, the ADPR compound for use in the compositions and methods provided herein is in the form of its sodium salt. In one embodiment, the ADPR compound is in the form of its monosodium salt. In another embodiment, the ADPR compound is in the form of its disodium salt.

In another specific embodiment, the ADPR compound for use in the compositions and methods provided herein is in the form of its lithium salt. In one embodiment, the ADPR compound is in the form of its monolithium salt. In another embodiment, the ADPR compound is in the form of its dilithium salt.

In certain embodiments, the adenovirus-related disease or condition is a disease or condition that affects any portion of the eye, ear, mouth, upper respiratory tract, or lower respiratory tract. In one embodiment, the adenovirus-related disease or condition is selected from, but not limited to, epi-bulbar disease, conjunctivitis, keratitis, kerato-conjunctivitis, corneal abrasion, ulcerative infectious keratitis, epithelial keratitis, stromal keratitis, uveitis, acute glaucoma, blepharitis, otitis media, otitis externa, gingivitis, mucositis, pharyngitis, tonsillitis, rhinitis, sinusitis, laryngitis, croup, tracheitis, bronchitis, bronchiolitis, bronchiolar pneumonia, pneumonia, exacerbation of asthma, exacerbation of chronic obstructive pulmonary disease, or exacerbation of emphysema.

In certain embodiments, the cancer is lung cancer, adenocarcinoma of the lung, non-small cell lung carcinoma, pancreatic cancer, pancreatic adenocarcinoma, glioma, glioblastoma multiforme, or acute myeloid leukemia.

In certain embodiments, ADPR, or a pharmaceutically acceptable salt, solvate, hydrate, tautomer, stereoisomer, isotopologue, pro-drug, or polymorph thereof, is administered by topical, oral, parenteral, mucosal, or inhalation route of administration. In one embodiment, ADPR as described herein is administered by topical administration. In one embodiment, the topical administration is to an interior cellular or tissue surface. In a specific embodiment, the topical administration to an interior cellular or tissue surface is by aerosolization, spray, oral delivery, infusion or similar method to any surface of the respiratory tract. In another specific embodiment, the topical administration to an interior cellular or tissue surface is by oral delivery, infusion, or enema to any surface of the gastrointestinal tract (e.g., from the mouth to the anus). In another specific embodiment, the topical administration to an interior cellular or tissue surface is by parenteral injection or infusion to any internal organ. In another embodiment, the topical administration is to an exterior cellular or tissue surface, including, but not limited to, the skin, eye, nail, hair, or ear.

In certain embodiments, ADPR, or a pharmaceutically acceptable salt, solvate, hydrate, tautomer, stereoisomer, isotopologue, pro-drug, or polymorph thereof, is administered in combination with another medicament. In certain embodiments, the other medicament is an antiviral compound or a metal salt. In some embodiments, the other medicament is cidofovir, acyclovir, or ganciclovir. In a specific embodiment, the other medicament is cidofovir. In certain embodiments, the other medicament is a lithium, zinc, cobalt, or copper salt. In certain embodiments, the other medicament is selected from the group consisting of lithium benzoate, lithium bromide, lithium chloride, lithium sulfate, lithium tetraborate, lithium acetate, zinc chloride, zinc sulfate, zinc bromide, cobalt chloride, cobalt bromide, copper bromide (CuBr$_2$), copper chloride (CuCl$_2$), and copper sulfate. In a specific embodiment, the other medicament is lithium chloride.

Provided herein is a compound having the formula:

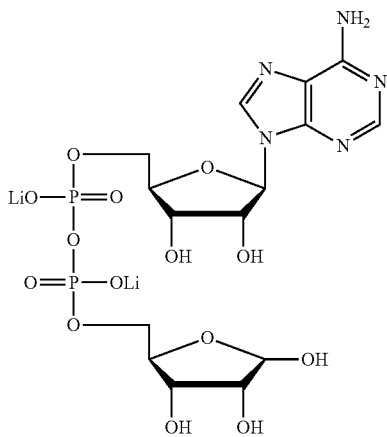

or a solvate, hydrate, tautomer, stereoisomer, isotopologue, pro-drug, or polymorph thereof.

In one aspect, provided herein are pharmaceutical compositions comprising (i) dilithium ADPR, or a solvate, hydrate, tautomer, stereoisomer, isotopologue, pro-drug, or polymorph thereof, and (ii) one or more pharmaceutically acceptable excipients; wherein the amount of dilithium ADPR in the pharmaceutical composition is in the range of about 0.001% w/w to about 10% w/w of the pharmaceutical composition.

In another aspect, provided herein are methods for treating, managing, or preventing cancer in a human patient, said method comprising administering to a patient having or at risk of developing cancer an effective amount of dilithium ADPR, or a solvate, hydrate, tautomer, stereoisomer, isotopologue, pro-drug, or polymorph thereof. In certain embodiments, the cancer is lung cancer, adenocarcinoma of the lung, non-small cell lung carcinoma, pancreatic cancer, pancreatic adenocarcinoma, glioma, glioblastoma multiforme, or acute myeloid leukemia.

4 BRIEF DESCRIPTION OF THE FIGURES

FIG. 2 depicts the plaque coverage (%) and the effects of ADPR (monosodium salt), nicotinamide, and cidofovir at various concentrations.

Figure 5:
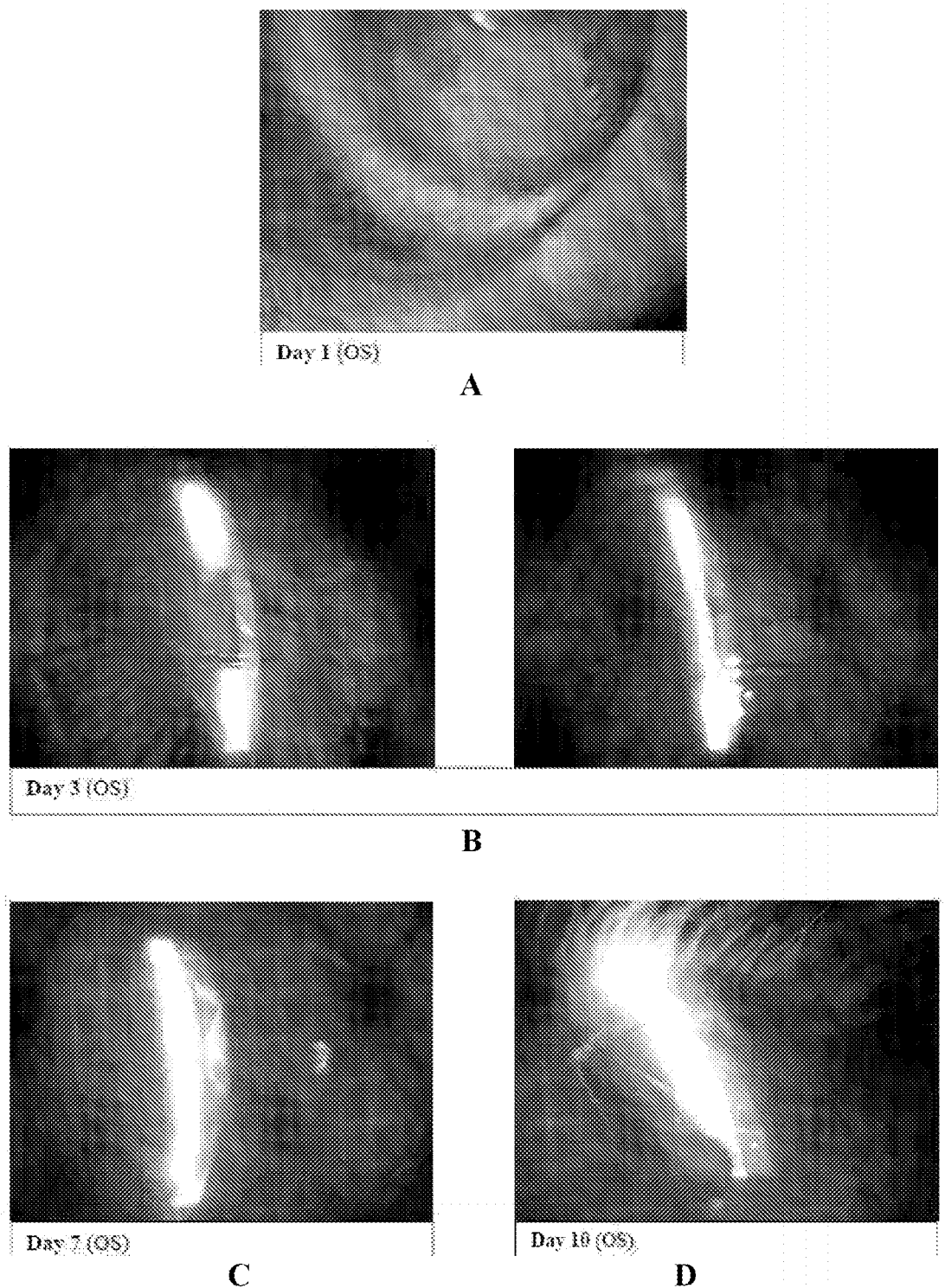

FIG. 5 shows representative images of the conjunctiva and cornea (slit lamp) from the left eye (OS is left eye and OD is right eye) for Group 1 animal P7278 which received no treatment. Only OS is evaluated as OD had a weak response to the adenovirus. Image A—Day 1 (OS): Congestion score of "2." Image B—Day 3 (OS): Deep corneal wound present with an increase in corneal opacity. Image C—Day 7 (OS): Increase in corneal opacity including the area of corneal scratches. Image D—Day 10 (OS): Decrease in opacity of scratches with general corneal opacities still present.

Figure 6:
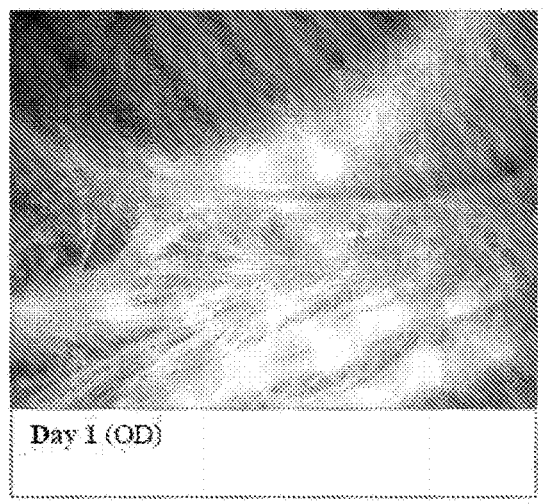
Figure 6:
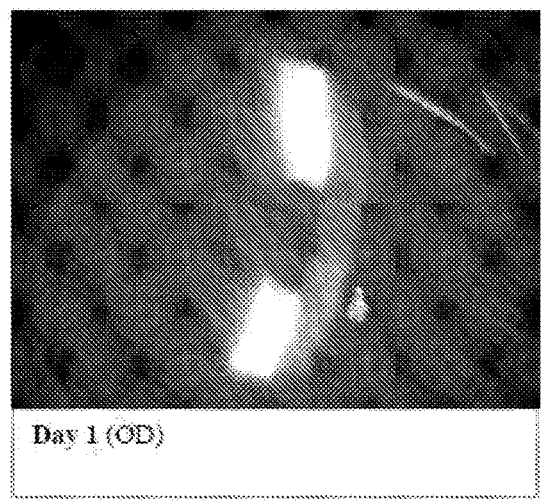
Figure 6:
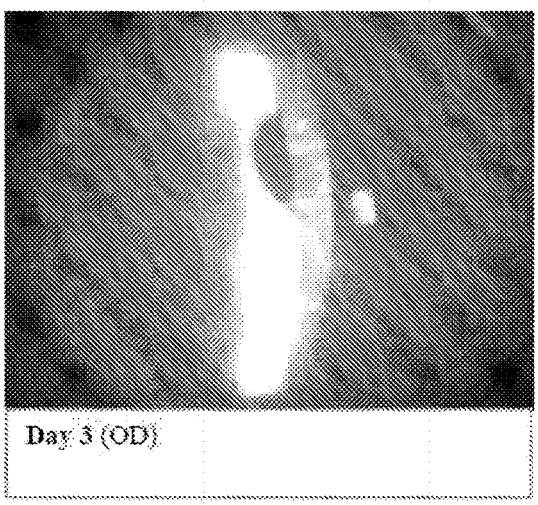
Figure 6:
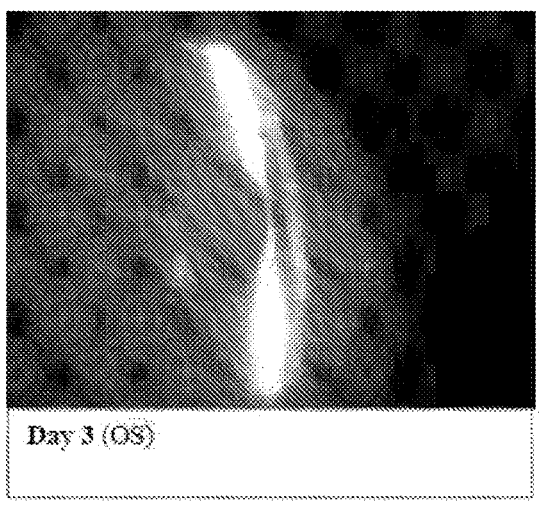
Figure 6:
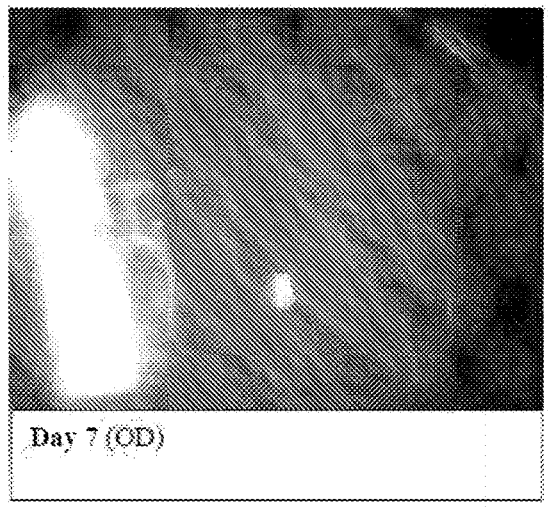
Figure 6:
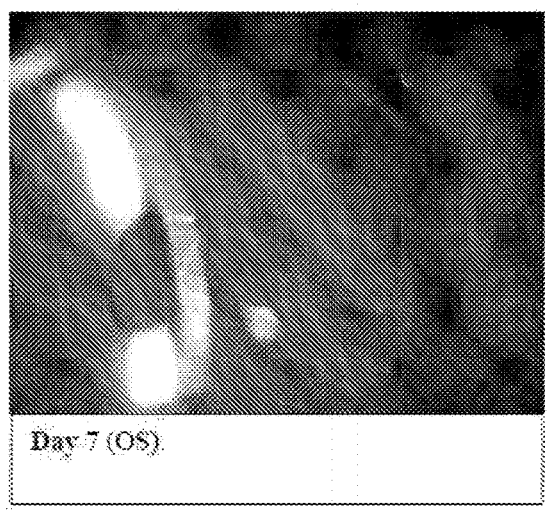
Figure 6:
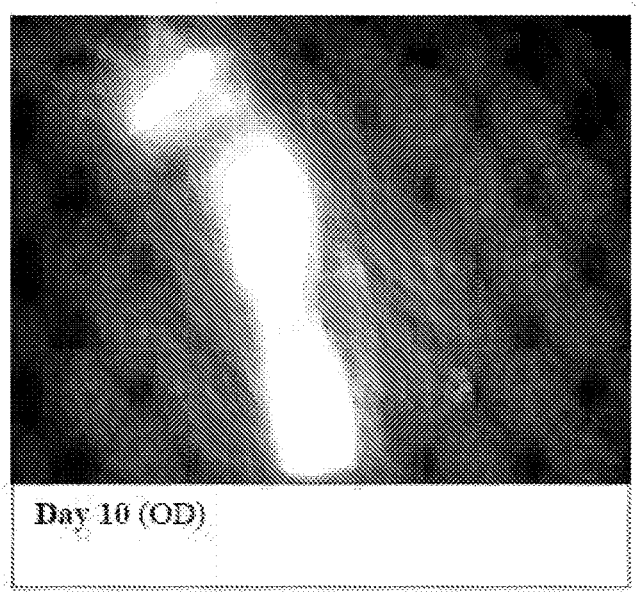

FIG. 6 shows representative images of the conjunctiva and cornea (slit lamp) from both eyes (OD is right eye and OS is left eye) for Group 2 animal P7279 which received treatment with the vehicle control. Image A—Day 1 (OD): Conjunctival discharge present. Image B—Day 1 (OD): Increase in opacities around corneal scratches. Image C—Day 3 (OD): Corneal scratch opacities increased. Image D—Day 3 (OS): Corneal scratch opacities increased. Image E—Day 7 (OD): Corneal scratch opacities increased. Image F—Day 7 (OS): Corneal scratch opacities slightly increased. Image G—Day 10 (OD): Corneal scratch opacities decreased.

Figure 7:
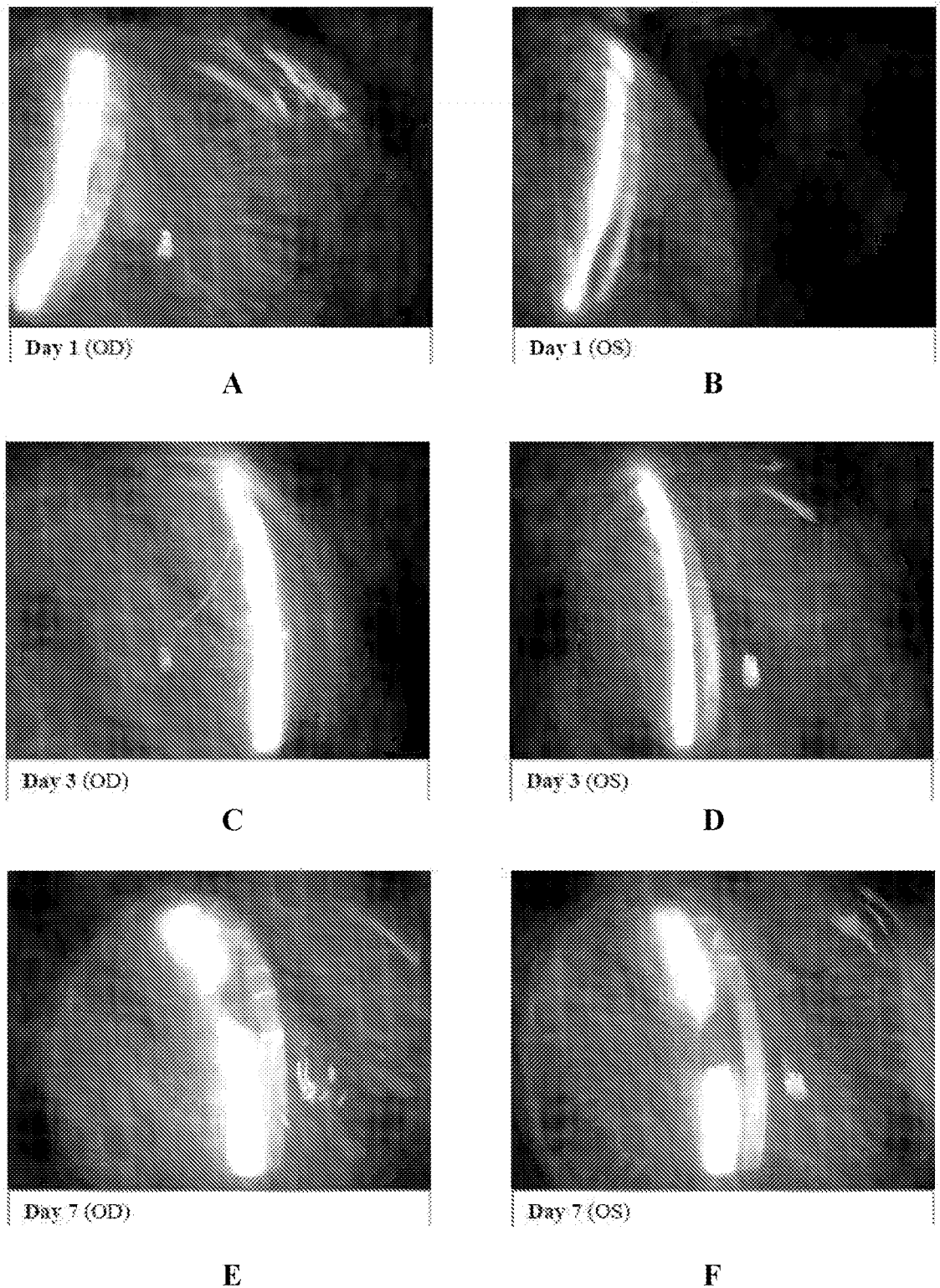
Figure 7:
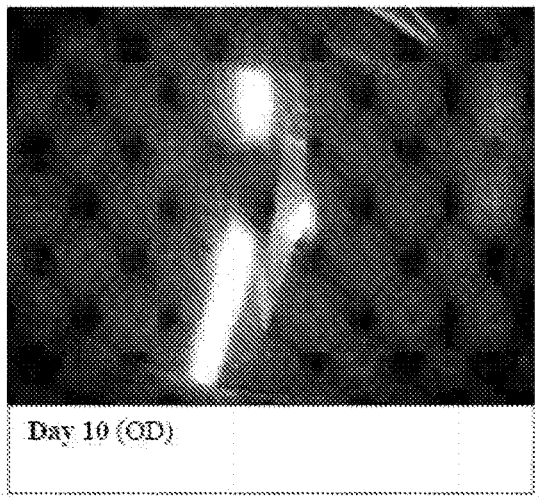
Figure 7:
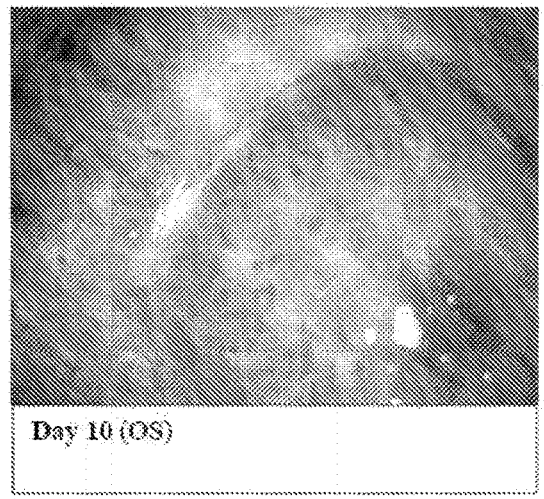
Figure 7:
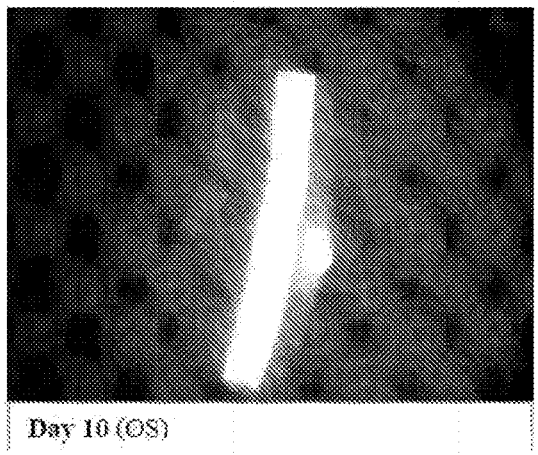
Figure 7:
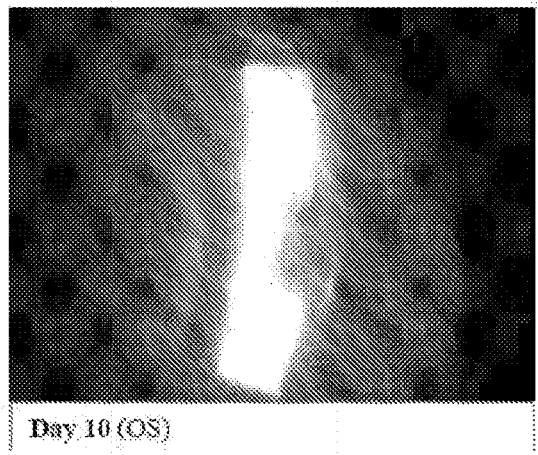

FIG. 7 shows representative images of the conjunctiva and cornea (slit lamp) from both eyes (OD is right eye and OS is left eye) for Group 3 animal P7280 which received treatment with the test article (2% ADPR, monosodium salt). Image A—Day 1 (OD): Corneal scratch opacities increased. Image B—Day 1 (OS): Corneal scratch opacities slightly increased. Image C—Day 3 (OD): Corneal scratch opacities decreased. Image D—Day 3 (OS): Corneal scratch opacities decreased. Image E—Day 7 (OD): The corneal scratch opacities and number of inflamed areas decreased. Image F—Day 7 (OS): Corneal scratch opacities decreased. Image G—Day 10 (OD): Corneal scratch opacities decreased. Image H—Day 10 (OS): Third eyelid congestion core of "2." Image I—Day 10 (OS): Scratches appeared healed over. Image J—Day 10 (OS): Corneal scratch opacities decreased.

Figure 8:
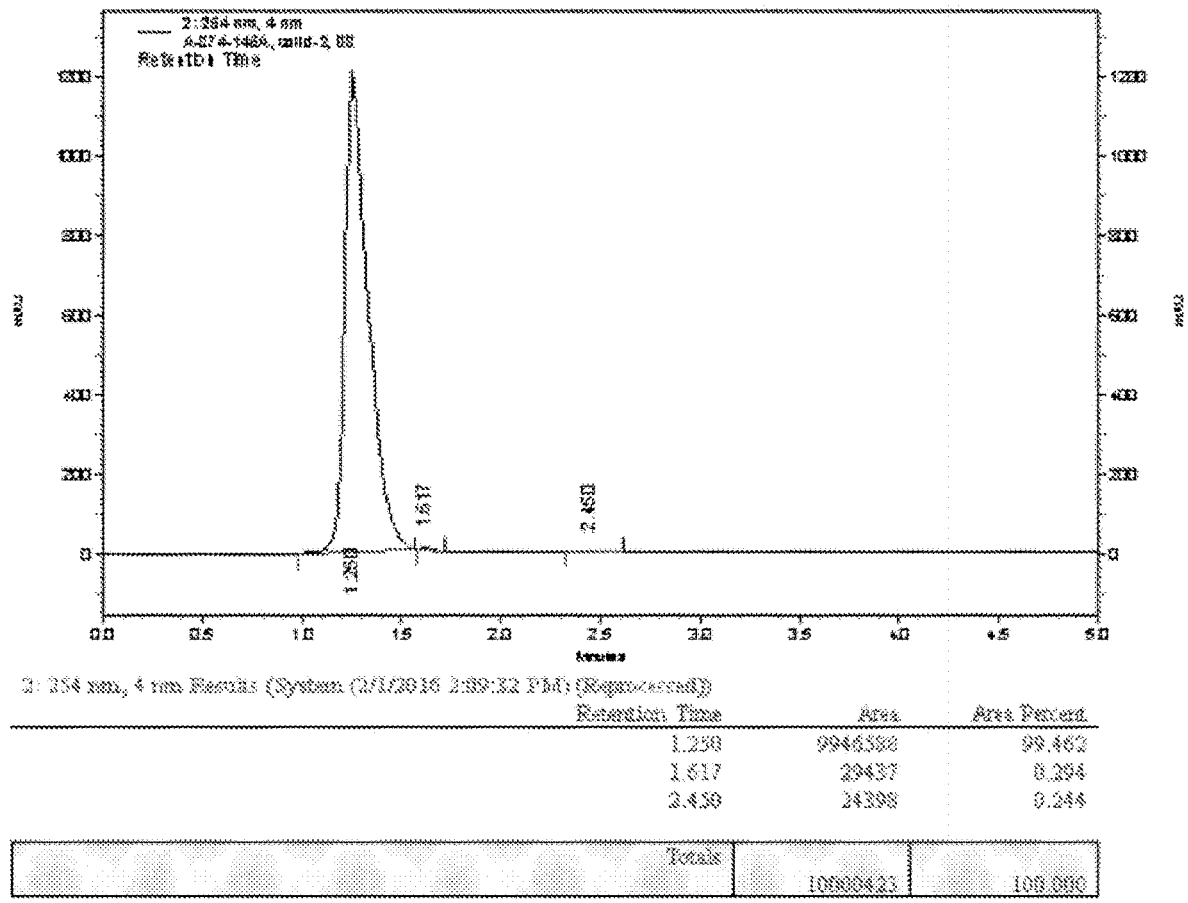

FIG. 8 shows an HPLC trace of dilithium ADPR synthesized as described in Example 4.

Figure 9:
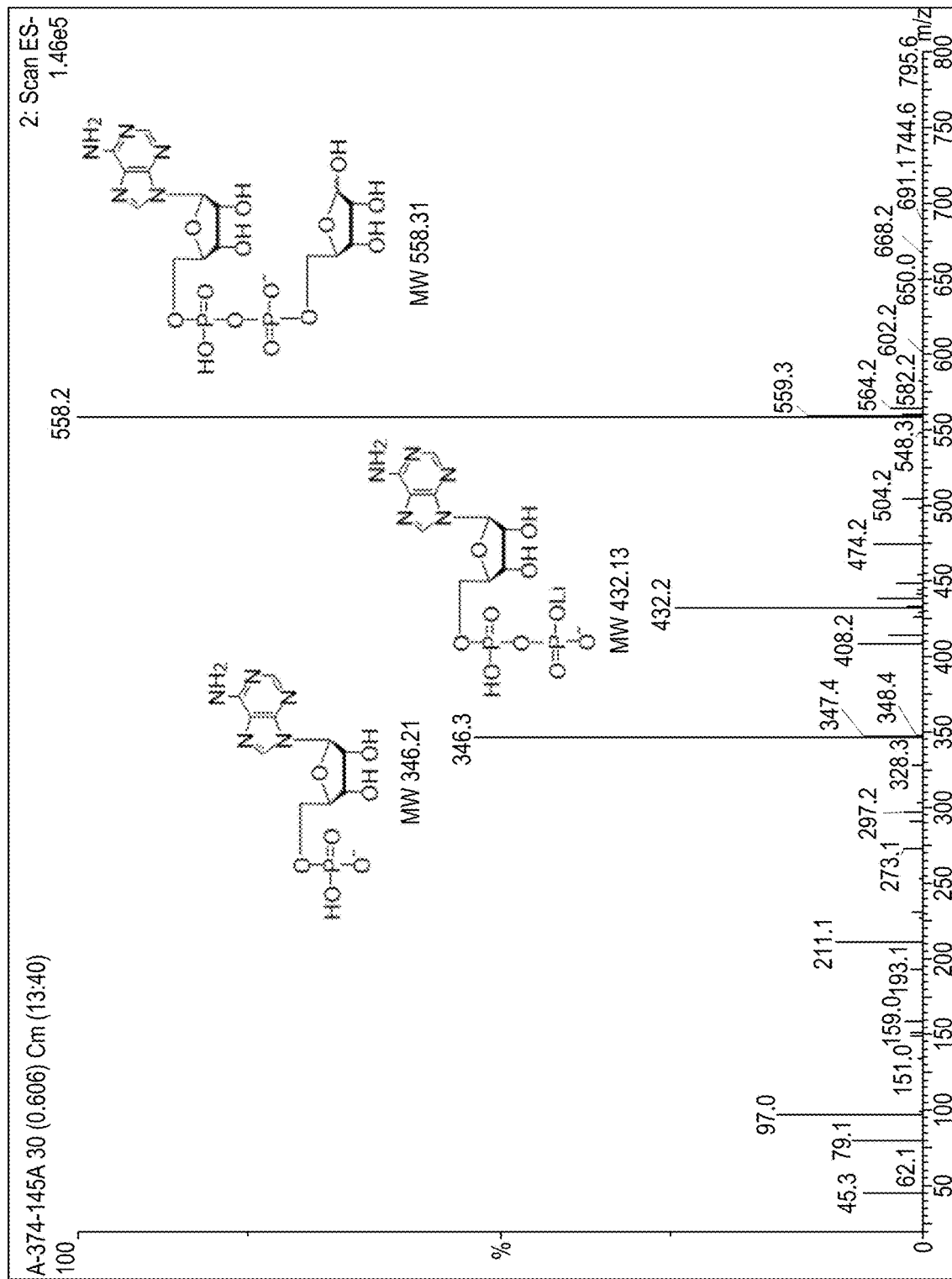

FIG. 9 shows mass spectrometry analysis of dilithium ADPR synthesized as described in Example 4.

Figure 10:
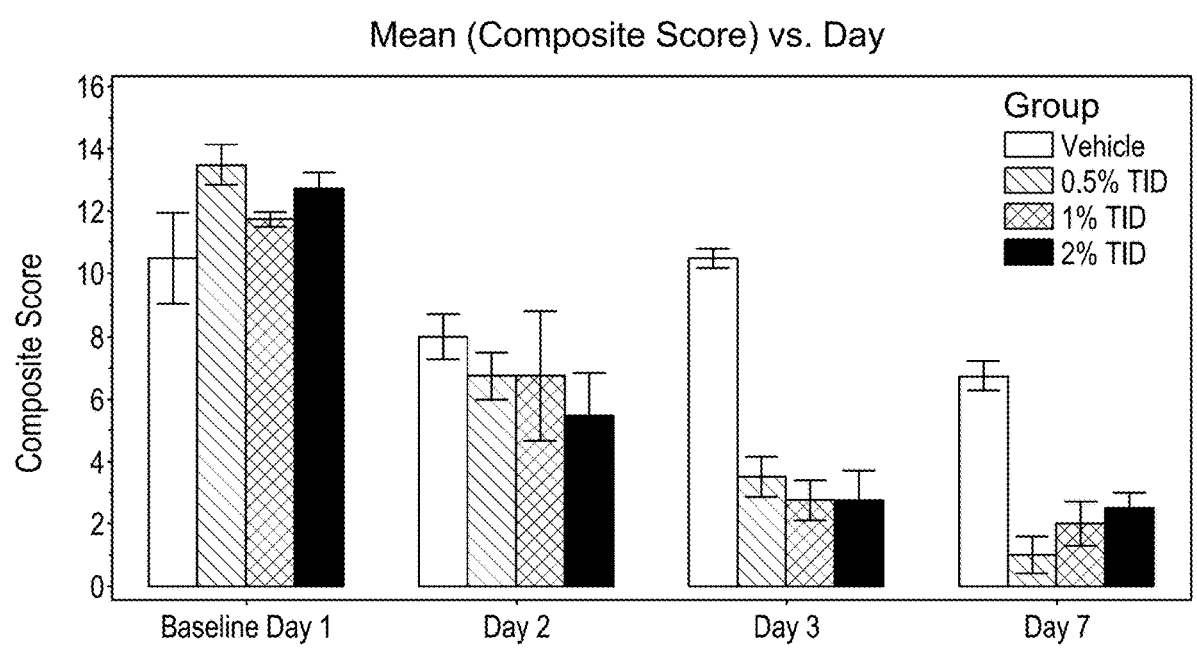

FIG. 10 shows the composite modified McDonald-Shadduck score (total of all sub scores) in rabbit eyes at baseline on Day 1 (24 hours following the second corneal scarification and inoculation with adenovirus, and just prior to the start of treatment), and following treatment on Day 2, Day 3, and Day 7. All three of the dilithium ADPR treated groups (0.5%, 1%, and 2% TID) demonstrated significant improvement ($p<0.01$) on Day 3 and Day 7 compared to baseline on Day 1. The vehicle treated group did not demonstrate significant change.

Figure 11:
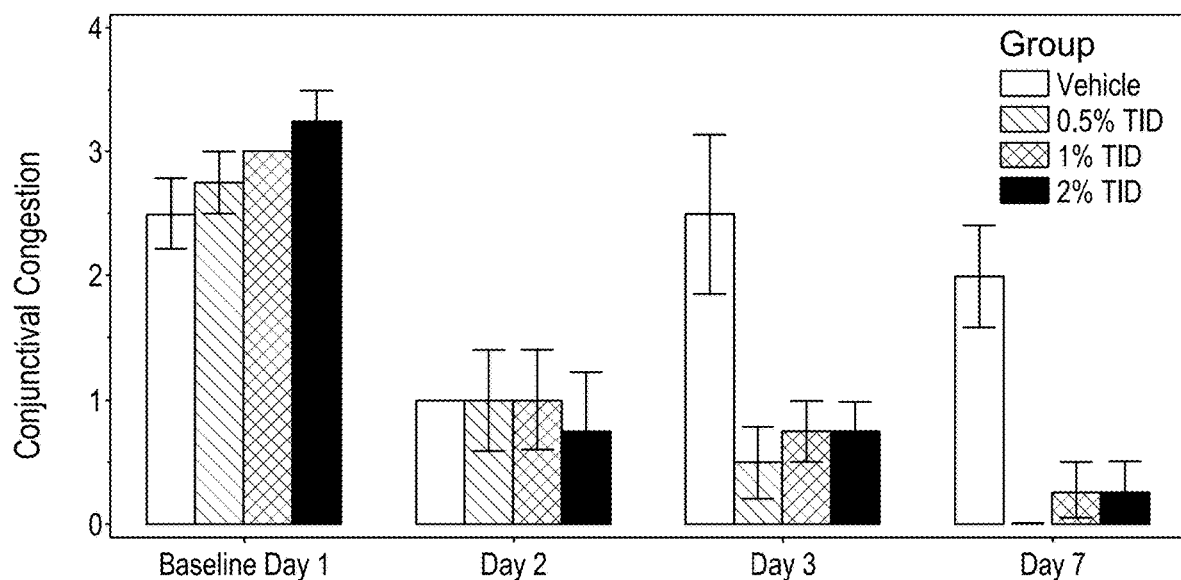
Figure 11:
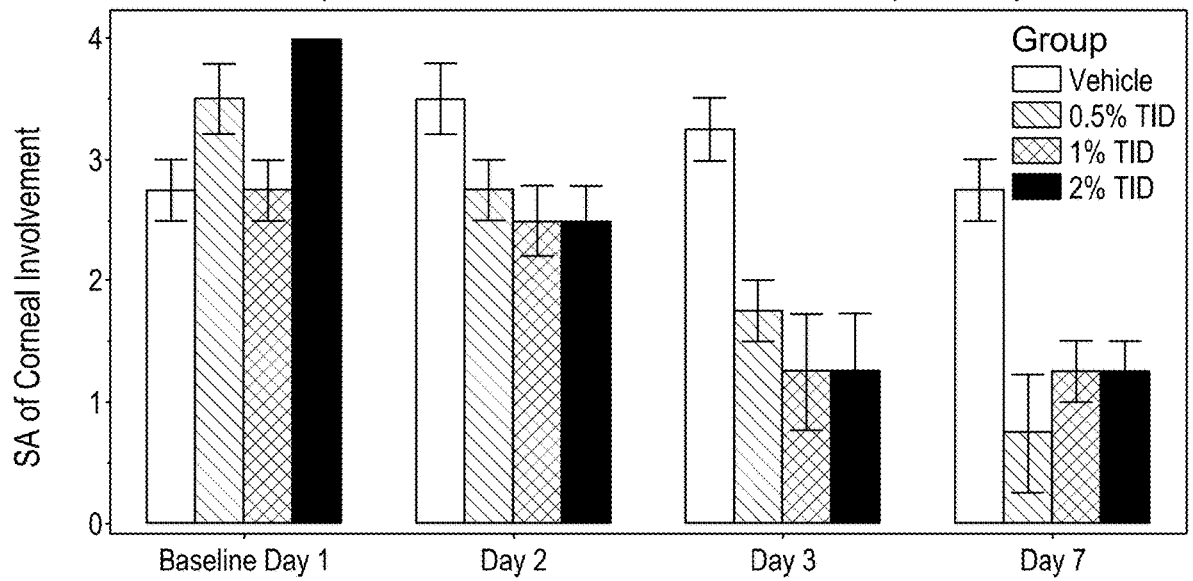

FIG. 11 shows the subscores for: conjunctival congestion (Image A), and surface area of corneal involvement (Image B) from the modified McDonald-Shadduck score in rabbit eyes at baseline on Day 1 (24 hours following the second corneal scarification and inoculation with adenovirus, and just prior to the start of treatment), and following treatment on Day 2, Day 3, and Day 7. For conjunctival congestion (Image A), all three of the treated groups (0.5%, 1%, and 2% TID) demonstrated significant improvement ($p<0.01$) on Day 3 and Day 7 compared to baseline on Day 1. The vehicle treated group did not demonstrate significant change. For surface area of corneal involvement (Image B), all three of the treated groups (0.5%, 1%, and 2% TID) demonstrated significant improvement ($p<0.05$) on Day 3 and Day 7 compared to baseline on Day 1. The vehicle treated group did not demonstrate significant change.

Figure 12:
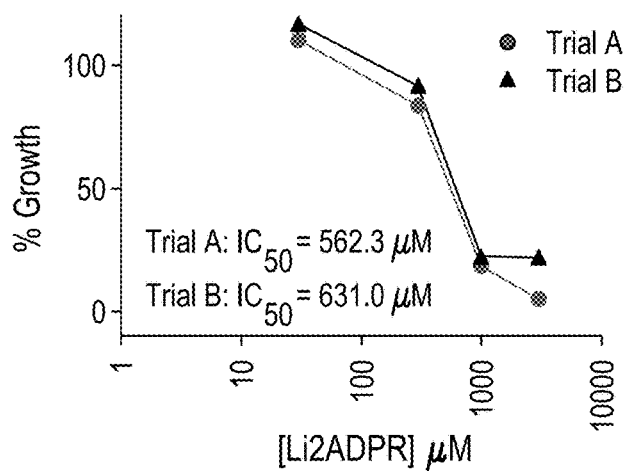
Figure 12:
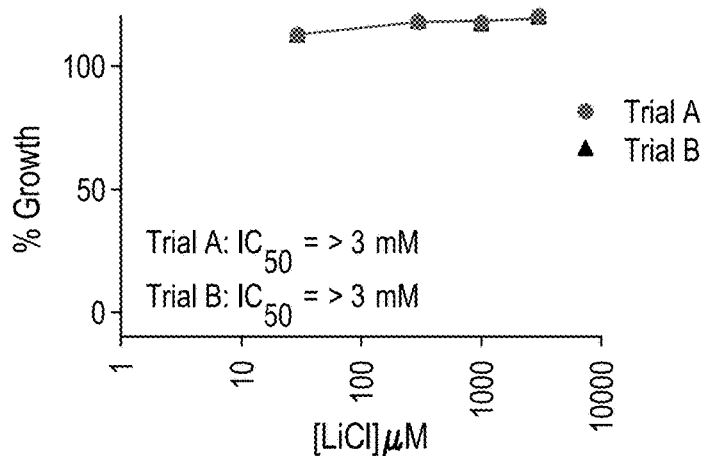
Figure 12:
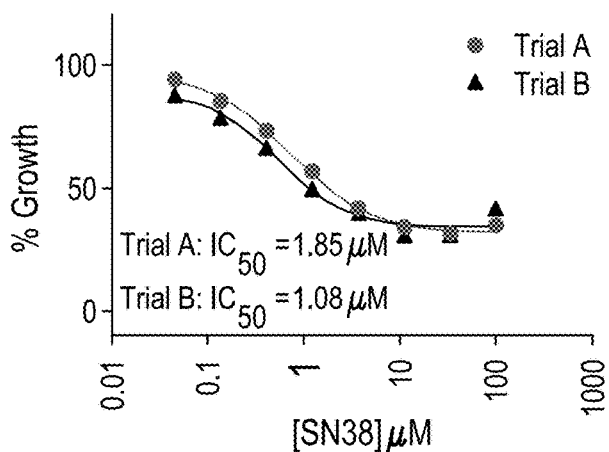

FIG. 12 shows percent cell growth relative to vehicle control for ASPC1 cells following treatment with increasing concentrations of: dilithium ADPR (Image A), LiCl (Image B), and SN38 (Image C).

Figure 13:
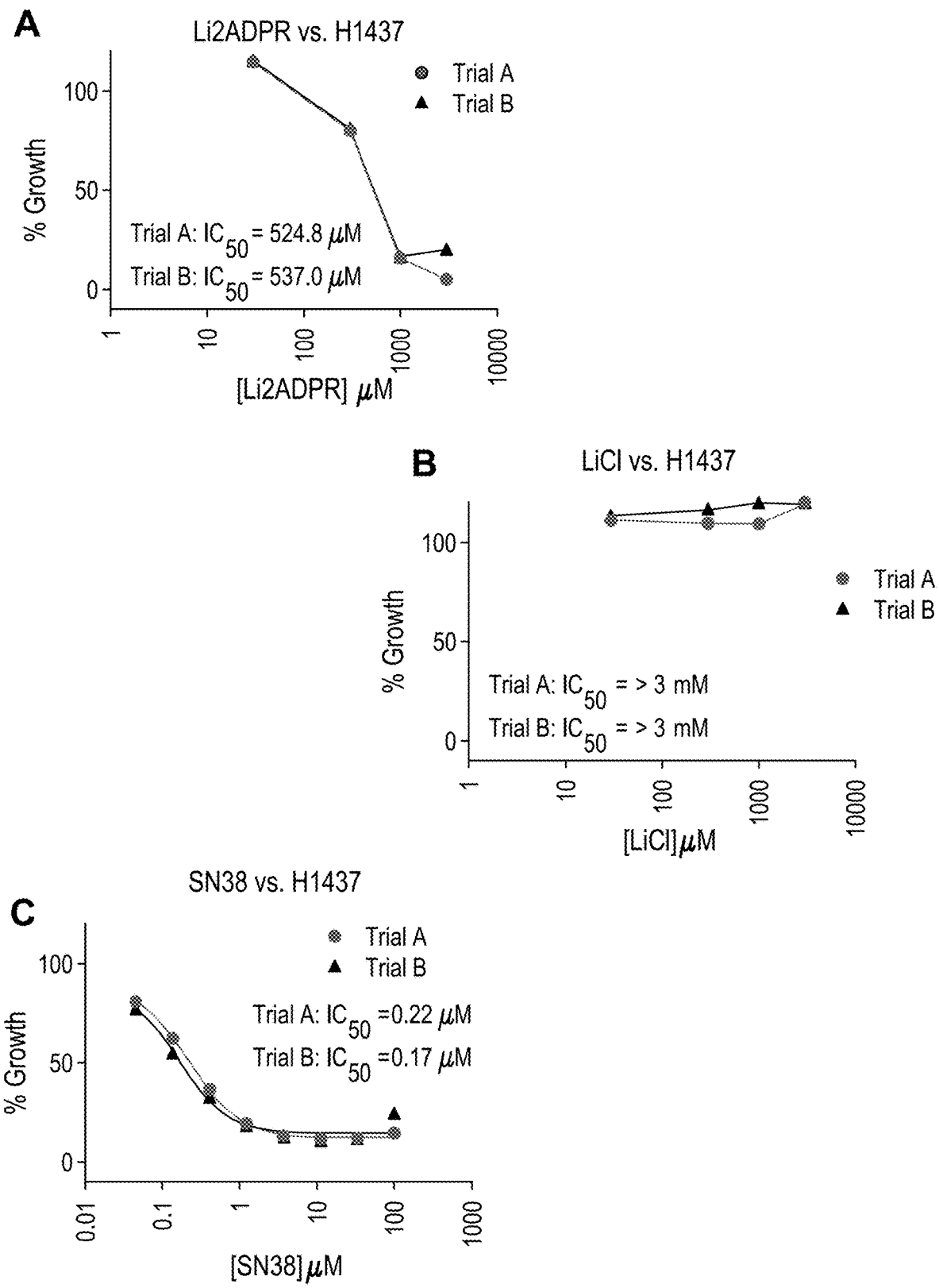

FIG. 13 shows percent cell growth relative to vehicle control for H1437 cells following treatment with increasing concentrations of: dilithium ADPR (Image A), LiCl (Image B), and SN38 (Image C).

Figure 14:
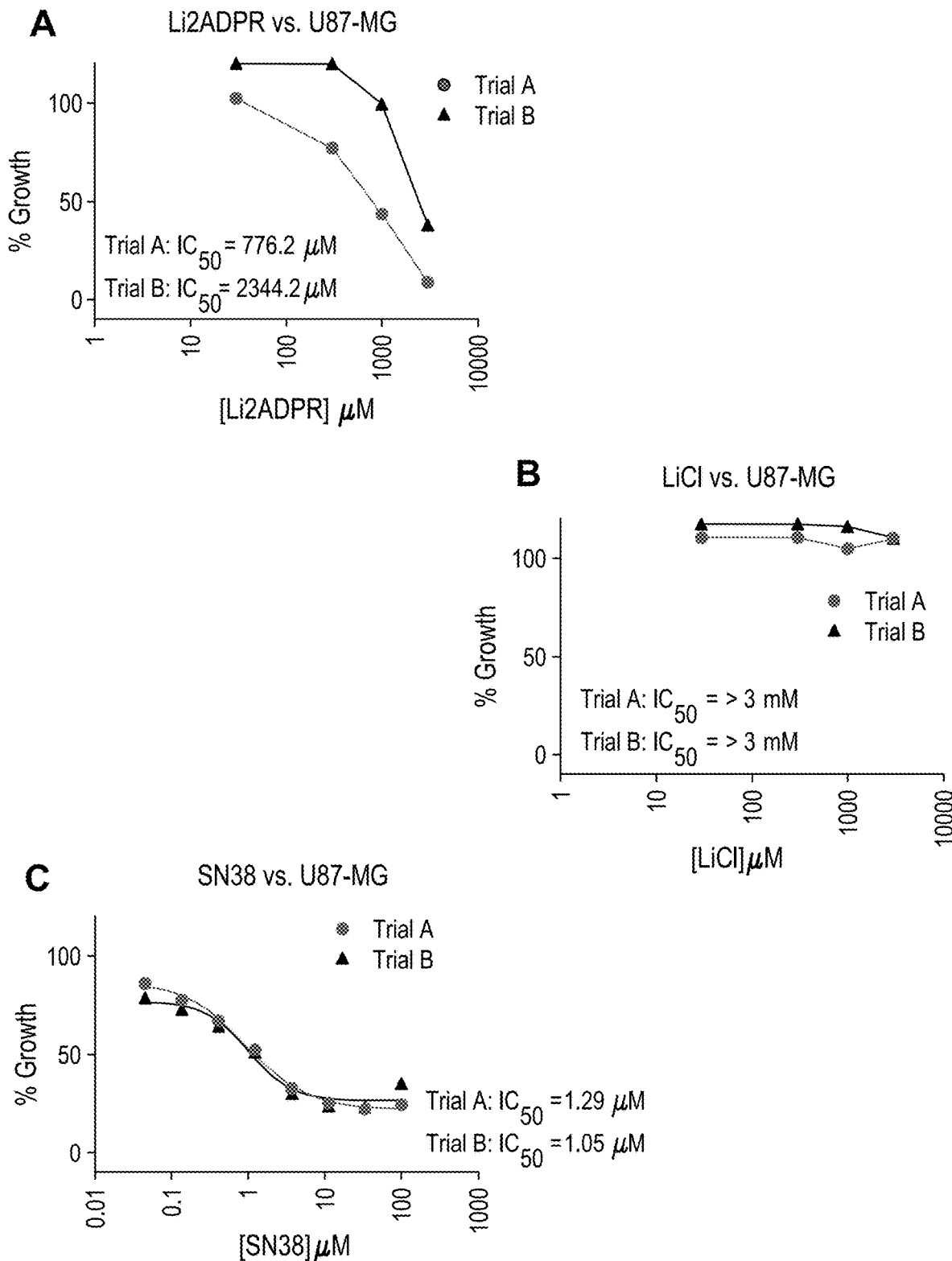

FIG. 14 shows percent cell growth relative to vehicle control for U87-MG cells following treatment with increasing concentrations of: dilithium ADPR (Image A), LiCl (Image B), and SN38 (Image C).

Figure 15:
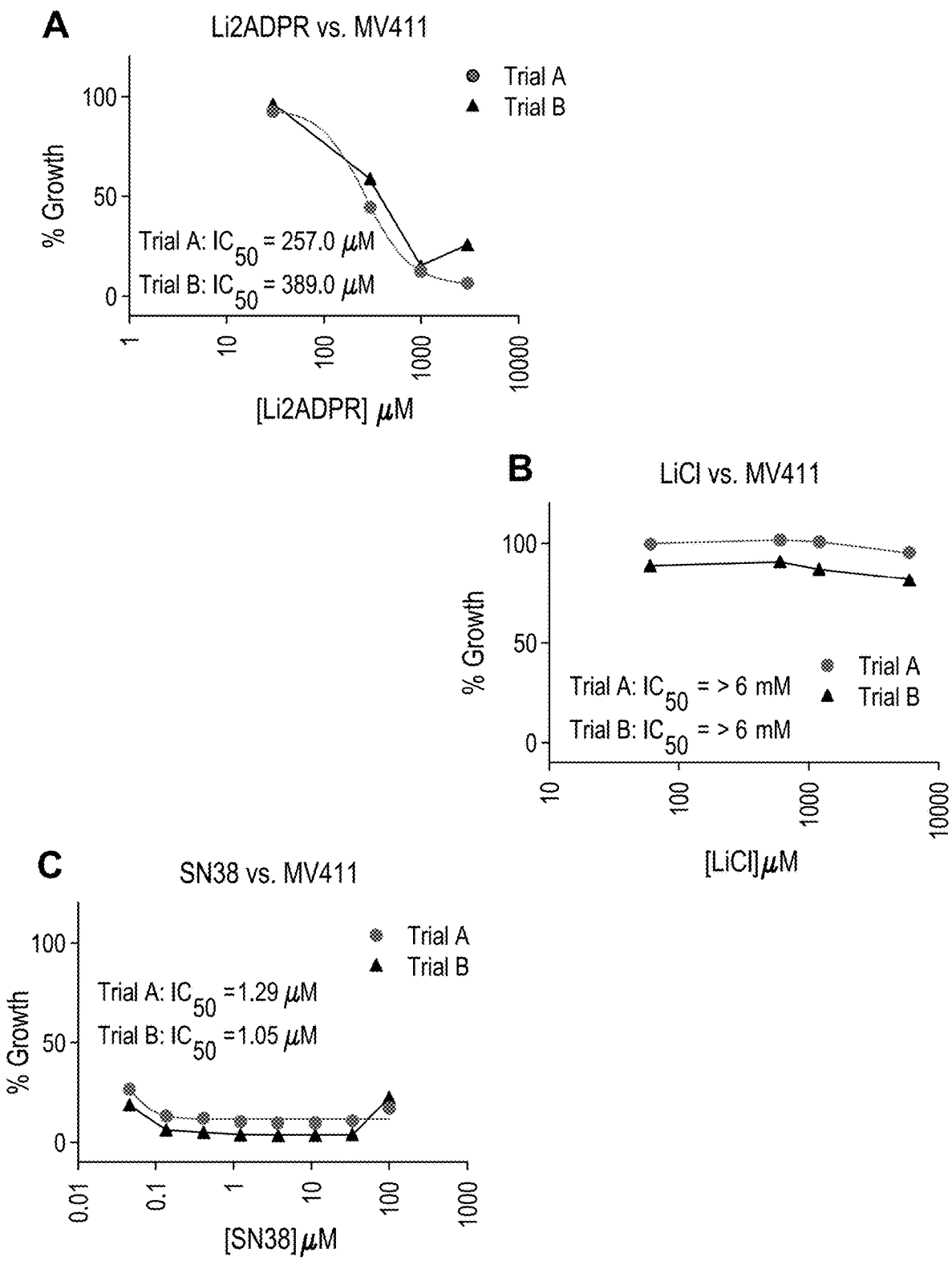

FIG. 15 shows percent cell growth relative to vehicle control for MV411 cells following treatment with increasing concentrations of: dilithium ADPR (Image A), LiCl (Image B), and SN38 (Image C).

5 DETAILED DESCRIPTION

5.1 Definitions

As used herein, the term "ADPR" is understood to include ADPR as well as a pharmaceutically acceptable salt, solvate, hydrate, tautomer, stereoisomer, isotopologue, pro-drug, or polymorph thereof.

As used herein, the term "dose(s)" means a quantity of ADPR, or a pharmaceutically acceptable salt, solvate, hydrate, tautomer, stereoisomer, isotopologue, pro-drug, or polymorph thereof, to be administered at one time. A dose may comprise a single unit dosage form, or alternatively may comprise more than a single unit dosage form (e.g., a single dose may comprise two tablets), or even less than a single unit dosage form (e.g., a single dose may comprise half of a tablet).

As used herein, the term "daily dose" means a quantity of ADPR, or a pharmaceutically acceptable salt, solvate, hydrate, tautomer, stereoisomer, isotopologue, pro-drug, or polymorph thereof that is administered in a 24 hour period. Accordingly, a daily dose may be administered all at once (i.e., once daily dosing) or alternatively the daily dosing may be divided such that administration of ADPR, or a pharmaceutically acceptable salt, solvate, hydrate, tautomer, stereoisomer, isotopologue, pro-drug, or polymorph thereof, is twice daily, three times daily, or even four times daily.

As used herein, the term "patient" or "subject" include animals, such as mammals, including, but not limited to, primates (e.g., humans), cows, sheep, goats, horses, dogs, cats, rabbits, rats, mice, monkeys, chickens, turkeys, quails, or guinea pigs and the like. In one embodiment, as used herein, the term "patient" or "subject" means a mammal. In one embodiment, as used herein, the term "patient" or "subject" means a human.

As used herein, an "effective amount" refers to that amount of ADPR, or a pharmaceutically acceptable salt, solvate, hydrate, tautomer, stereoisomer, isotopologue, pro-drug, or polymorph thereof that is sufficient to provide a therapeutic benefit in the treatment of the disease or to delay or minimize symptoms associated with the disease. In certain embodiments the disease is an adenovirus-related disease or condition. In certain embodiments, the disease is cancer. In certain embodiments, the disease is an eye disorder. In certain embodiments, the disease is a disease or condition caused by infection, inflammation, or physical, chemical, thermal, or radiation injuries. In certain embodiments, the disease is a disease or condition affecting plants and/or crops.

As used herein, the terms "prevent", "preventing" and "prevention" are art-recognized, and when used in relation to a condition, such as an adenovirus-related disease or condition, an eye disorder, cancer, or a disease or condition caused by infection, inflammation, or physical, chemical, thermal, or radiation injuries, or any other medical condition, such as those described herein, is well understood in the art, and includes administration of a compound which reduces the frequency of, or delays the onset of, symptoms of a medical condition in a subject relative to a subject which does not receive the composition.

As used herein, the terms "treat", "treating" and "treatment" refer to the reversing, reducing, or arresting the symptoms, clinical signs, and underlying pathology of a condition in manner to improve or stabilize a subjects condition. The terms "treat" and "treatment" also refer to the eradication or amelioration of the disease or symptoms associated with the disease. In certain embodiments, such terms refer to minimizing the spread or worsening of the disease resulting from the administration of a compound as disclosed herein to a patient with such a disease. In certain embodiments the disease is an adenovirus-related disease or condition. In certain embodiments, the disease is cancer. In certain embodiments, the disease is an eye disorder. In certain embodiments, the disease is a disease or condition caused by infection, inflammation, or physical, chemical, thermal, or radiation injuries.

As used herein, the term "pharmaceutical composition" refers to compositions suitable for use or prescribed treatment in treating, managing, or preventing an adenovirus-related disease or condition, an eye disorder, cancer, or a disease or condition caused by infection, inflammation, or physical, chemical, thermal, or radiation injuries.

As used herein, the term "pharmaceutically acceptable salt" refers to those salts that are, within the scope of sound medical judgment, suitable for use in contact with the human tissue without undue toxicity, irritation, allergic response and the like and are commensurate with a reasonable benefit/risk ratio.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 15%, 10%, 9%, 8%, 7%, 6%, 5%, 4%, 3%, 2%, 1%, 0.5%, or 0.05% of a given value or range.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The compositions and methods of the present invention can comprise, consist of, or consist essentially of the essential elements and limitations of the invention described herein, as well as any additional or optional ingredients, components, or limitations described herein or otherwise useful in compositions and methods of the general type as described herein.

5.2 5'-adenosine diphosphate ribose (ADPR)

The uses and compositions provided herein relate to 5'-adenosine diphosphate ribose (ADPR; ADP-ribose; adenosine 5'-(trihydrogen diphosphate),P'→5-ester with D-ribose; adenosine 5'-(trihydrogen pyrophosphate),5'→5-ester with D-ribofuranose; adenosine 5'-diphosphate, D-ribose ester; adenosine 5'-pyrophosphate, 5'→5-ester with D-ribofuranose; ribofuranose, 5-(adenosine 5'-pyrphosphoryl)-D-ribose; adenosine 5'-diphosphoribose; adenosine diphosphate ribose; adenosine diphosphoribose; adenosine pyrophosphate-ribose; ribose adenosinediphosphate).

ADPR is a naturally occurring small molecule well known in the chemical literature. It is often characterized by the general formula $C_{15}H_{23}N_5O_{14}P_2$, and includes, for example, various salts such as sodium salt corresponding to the following general structure of formula (I):

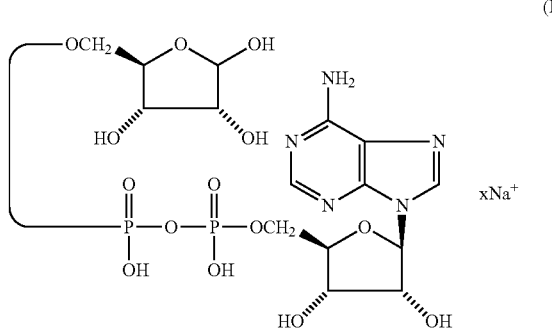

(I)

ADPR can be readily prepared by methods well known in the chemical arts. It is also commercially available as a purified raw material, an example of which can be purchased from Sigma or Sigma-Aldrich Co.

The ADPR compound for use in the compositions and methods provided herein includes any known or pharmaceutically acceptable salt thereof, non-limiting examples of which include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate, undecanoate, or combinations thereof.

The ADPR compound can also include those derivatives in which basic nitrogen-containing groups are quaternized with materials such as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; aryl alkyl halides like benzyl and phenethyl bromides and many others.

Examples of acids which may be employed to form pharmaceutically acceptable acid addition salts of ADPR include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of the ADPR by reacting an acidic moiety with a suitable base such as, but not limited to, the hydroxide, carbonate or bicarbonate of a pharmaceutically acceptable metal ion or with ammonia or an organic primary, secondary or tertiary amine. Non-limiting examples of pharmaceutically acceptable salts include those based on alkali metals, alkaline earth metals, transition metals, or post-transition metals, such as lithium (including dilithium), sodium, potassium, calcium, magnesium, aluminum, zinc, cobalt, and copper salts and the like, and nontoxic quaternary ammonia and amine captions including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine, and the like.

In one embodiment, the ADPR compound for use in the compositions and methods provided herein is synthesized via the hydrolysis of nicotinamide adenine dinucleotide (NAD+) in the presence of an alkaline base, such as, but not limited to, lithium hydroxide or sodium hydroxide. In such an embodiment, the ADPR thus synthesized is isolated in the form of its mono or di salt of the metal ion of the corresponding base.

In a specific embodiment, the ADPR compound for use in the compositions and methods provided herein is in the form of its sodium salt. In one embodiment, the ADPR compound is in the form of its monosodium salt. In another embodiment, the ADPR compound is in the form of its disodium salt.

In another specific embodiment, the ADPR compound for use in the compositions and methods provided herein is in the form of its lithium salt. In one embodiment, the ADPR compound is in the form of its monolithium salt. In another embodiment, the ADPR compound is in the form of its dilithium salt.

Further provided herein are pro-drugs of ADPR, or pharmaceutically acceptable salts or stereoisomers thereof. Such pro-drugs provide a longer half-life and wider tissue distribution following administration of the drug, for example, through intravenous, cerebral spinal fluid, or other fluid compartment infusion or injection.

In one embodiment, the pro-drug is poly-ADPR (with or without an acceptor protein, peptide, or amino acid). In such a pro-drug concept, the poly-ADPR is used as depot form of ADPR, such that ADPR is released slowly by hydrolases in the blood, peritoneal fluid, cerebral spinal fluid, vitreous, aqueous humor, subcutaneous fluid, interstitial fluid, and other non-intracellular spaces to treat ADPR responsive diseases. The general structure of a representative poly-ADPR pro-drug (with an acceptor protein) is represented by formula (II):

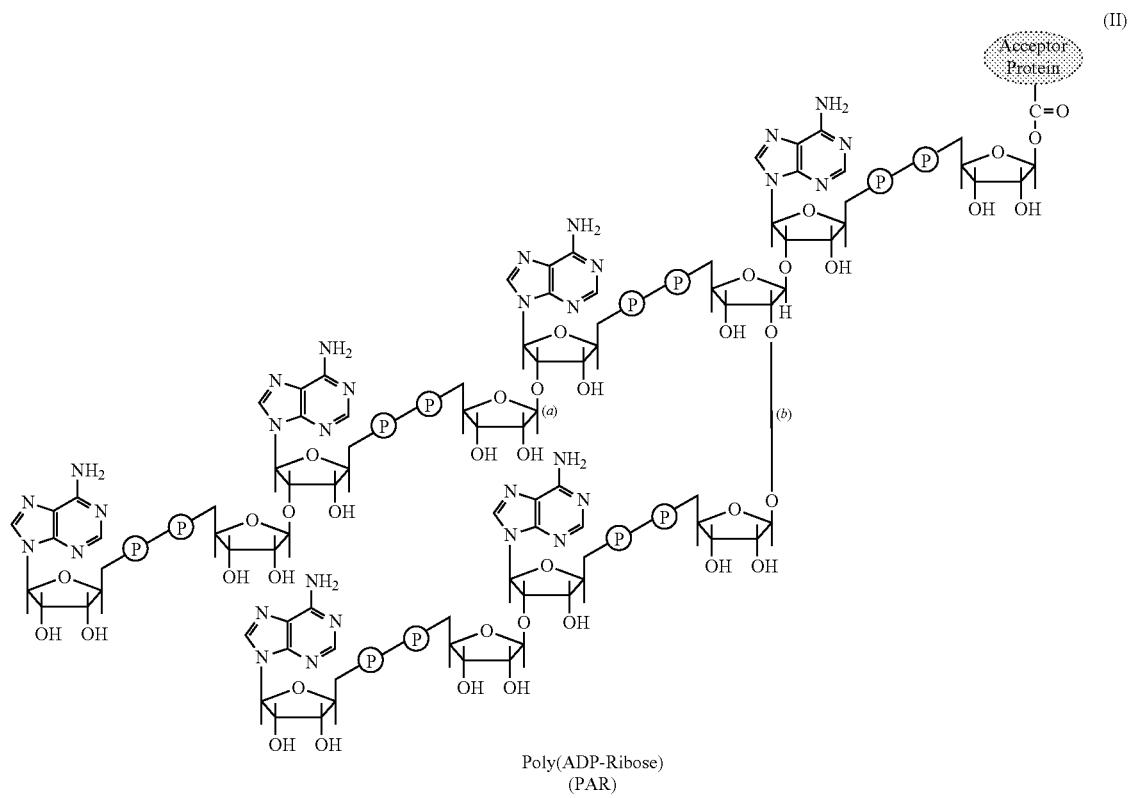

Poly(ADP-Ribose)
(PAR)

In certain embodiments, the pro-drug of ADPR is ADPR condensed with one or more molecules of a carboxylic acid, amino acid, fatty acid, or any combinations thereof. In one embodiment, ADPR is condensed at one or more of the hydroxyl groups in the terminal ribose moiety, for example, as represented by the general structure of formula (III). Examples of fatty acids that can be used in preparing ADPR pro-drugs include, but are not limited to, palmitic acid, linolenic acid, stearic acid, oleic acid, and others. Examples of carboxylic acids that can be used in preparing ADPR pro-drugs include, but are not limited to, 3-oxopentanoic acid, 3-hydroxypentanoic acid, acetoacetic acid, and beta-hydroxybutyric acid. Examples of amino acids that can be used in preparing ADPR pro-drugs include, but are not limited to, glutamic acid, aspartic acid, lysine, and arginine.

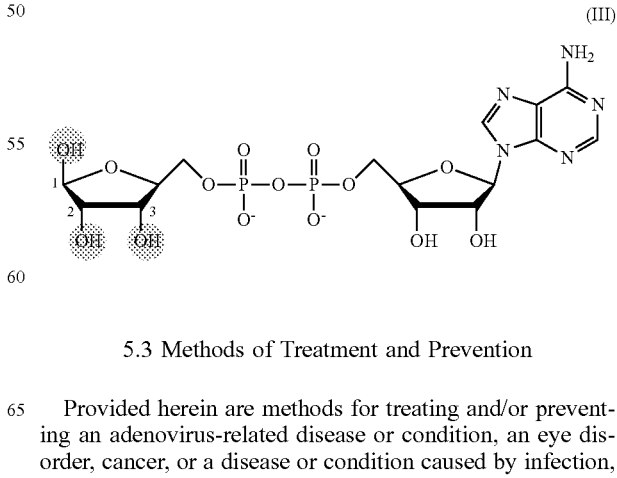

5.3 Methods of Treatment and Prevention

Provided herein are methods for treating and/or preventing an adenovirus-related disease or condition, an eye disorder, cancer, or a disease or condition caused by infection, inflammation, or physical, chemical, thermal, or radiation injuries, comprising administering ADPR or a pharmaceutically acceptable salt, solvate, hydrate, tautomer, stereoisomer, isotopologue, pro-drug, or polymorph thereof, or a pharmaceutical composition thereof, to a patient having or at risk of developing an adenovirus-related disease or condition, an eye disorder, cancer, or a disease or condition caused by infection, inflammation, or physical, chemical, thermal, or radiation injuries.

In certain embodiments, provided herein are methods for treating or preventing an adenovirus-related disease or condition, an eye disorder, cancer, or a disease or condition caused by infection, inflammation, or physical, chemical, thermal, or radiation injuries, comprising administering to a patient having or at risk of developing an adenovirus-related disease or condition, an eye disorder, cancer, or a disease or condition caused by infection, inflammation, or physical, chemical, thermal, or radiation injuries, a pharmaceutically effective amount of ADPR, or a pharmaceutically acceptable salt, solvate, hydrate, tautomer, stereoisomer, isotopologue, pro-drug, or polymorph thereof.

In certain embodiments, provided herein are methods for treating or preventing an adenovirus-related disease or condition, comprising administering to a patient having an adenovirus-related disease or condition, or to a patient at risk of developing an adenovirus-related disease or condition, a pharmaceutically effective amount of ADPR, or a pharmaceutically acceptable salt, solvate, hydrate, tautomer, stereoisomer, isotopologue, pro-drug, or polymorph thereof, wherein the adenovirus-related disease or condition is a disease or condition that affects any portion of the eye, ear, mouth, upper respiratory tract, or lower respiratory tract. In some embodiments, the adenovirus-related disease or condition is selected from, but not limited to, epi-bulbar disease, conjunctivitis, keratitis, kerato-conjunctivitis, corneal abrasion, ulcerative infectious keratitis, epithelial keratitis, stromal keratitis, uveitis, acute glaucoma, blepharitis, otitis media, otitis externa, gingivitis, mucositis, pharyngitis, tonsillitis, rhinitis, sinusitis, laryngitis, croup, tracheitis, bronchitis, bronchiolitis, bronchiolar pneumonia, pneumonia, exacerbation of asthma, exacerbation of chronic obstructive pulmonary disease, or exacerbation of emphysema. In certain embodiments, the adenovirus-related disease or condition is conjunctivitis, keratitis, kerato-conjunctivitis, pharyngitis, tonsillitis, laryngitis, rhinitis, sinusitis, bronchitis, bronchiolitis, or pneumonia. In one embodiment, the adenovirus-related disease or condition is keratitis, conjunctivitis, or keratoconjunctivitis. In another embodiment, the adenovirus-related disease or condition is bronchitis or bronchiolitis. In another embodiment, the adenovirus-related disease or condition is pharyngitis, tonsillitis, or laryngitis.

In certain embodiments, provided herein are methods for treating or preventing an adenovirus-related disease or condition, an eye disorder, cancer, or a disease or condition caused by infection, inflammation, or physical, chemical, thermal, or radiation injuries, comprising administering to a patient having, or at risk of developing, an adenovirus-related disease or condition, an eye disorder, cancer, or a disease or condition caused by infection, inflammation, or physical, chemical, thermal, or radiation injuries, or a pharmaceutically effective amount of ADPR, or a pharmaceutically acceptable salt, solvate, hydrate, tautomer, stereoisomer, isotopologue, pro-drug, or polymorph thereof, wherein the ADPR compound is administered by topical, oral, parenteral, mucosal, or inhalation route of administration. In one embodiment, ADPR as described herein is administered by topical administration. In one embodiment, the topical administration is to an interior cellular or tissue surface. In a specific embodiment, the topical administration to an interior cellular or tissue surface is by aerosolization, spray, oral delivery, infusion or similar method to any surface of the respiratory tract. In another specific embodiment, the topical administration to an interior cellular or tissue surface is by oral delivery, infusion, or enema to any surface of the gastrointestinal tract (e.g., from the mouth to the anus). In another specific embodiment, the topical administration to an interior cellular or tissue surface is by parenteral injection or infusion to any internal organ. In another embodiment, the topical administration is to an exterior cellular or tissue surface, including, but not limited to, the skin, eye, nail, hair, or ear.

In certain embodiments, provided herein are methods for treating and/or prophylaxis of an eye disorder or a microorganism infection of at least one tissue of the eye, comprising administering to the eye of a patient one of more doses of the pharmaceutical composition provided herein. In one embodiment, the prophylaxis is prophylaxis of infection following corneal abrasion or ocular surgery. In a specific embodiment, the ADPR is in the form of its dilithium salt.

In one embodiment, the eye disorder affects any region of the anterior segment of the eye including, but not limited to, the cornea, conjunctiva, iris, aqueous humor (anterior chamber), lens, pupil, ciliary body and muscle, suspensory ligament, sclera, Schlemm's canal, and Zinn's zonule.

In one embodiment, the eye disorder is selected from the group consisting of a microorganism infection of at least one tissue of the eye, conjunctivitis, keratitis, kerato-conjunctivitis, corneal abrasion, ulcerative infectious keratitis, epithelial keratitis, stromal keratitis, uveitis, acute glaucoma, and blepharitis. In a specific embodiment, the eye disorder is infectious keratoconjunctivitis.

In one embodiment, the microorganism is a bacteria, virus, fungi, or amoebae. In one embodiment, the bacteria is mycobacteria.

In certain embodiments, provided herein are methods for treating and/or preventing a disease or condition caused by infection, physical injury, or inflammation, said method comprising administering ADPR or a pharmaceutically acceptable salt, solvate, hydrate, tautomer, stereoisomer, isotopologue, pro-drug, or polymorph thereof, or a pharmaceutical composition thereof, to a patient having or at risk of developing said disease or condition. In a specific embodiment, the disease or condition is caused by infection, physical injury, or inflammation of the cornea and/or conjunctiva. In a specific embodiment, the ADPR is in the form of its dilithium salt.

In certain embodiments, provided herein are methods for treating and/or preventing a disease or condition caused by physical, chemical, thermal, or radiation injury, said method comprising administering ADPR or a pharmaceutically acceptable salt, solvate, hydrate, tautomer, stereoisomer, isotopologue, pro-drug, or polymorph thereof, or a pharmaceutical composition thereof, to a patient having or at risk of developing said disease or condition. In a specific embodiment, the ADPR is in the form of its dilithium salt.

In another aspect of the invention, provided herein are methods for treating and/or preventing cancer, comprising administering ADPR or a pharmaceutically acceptable salt, solvate, hydrate, tautomer, stereoisomer, isotopologue, pro-drug, or polymorph thereof, or a pharmaceutical composition thereof, to a patient having or at risk of developing cancer. In a specific embodiment, the ADPR is in the form of its dilithium salt.

In certain embodiments, provided herein are methods for treating or preventing cancer, comprising administering to a patient having cancer, or to a patient at risk of developing cancer, a pharmaceutically effective amount of ADPR, or a pharmaceutically acceptable salt, solvate, hydrate, tautomer, stereoisomer, isotopologue, pro-drug, or polymorph thereof. In a specific embodiment, the ADPR is in the form of its dilithium salt.

As used herein, and unless otherwise specified, the terms "cancer" refers to or describes the physiological condition in mammals that is typically characterized by unregulated cell growth. Examples of cancer include solid tumors and hematological cancer. In some embodiments, the cancer is a primary cancer, in others, the cancer is metastasized.

As used herein "solid tumors" includes, but is not limited to, bladder cancer (including, but not limited to, superficial bladder cancer), breast cancer (including, but not limited to, luminal B type, ER+, PR+ and Her2+ breast cancer), central nervous system cancer (including, but not limited to, glioblastoma multiforme (GBM), glioma, medulloblastoma, and astrocytoma), colorectal cancer, gastrointestinal cancer (including, but not limited to, stomach cancer, oesophagus cancer, and rectum cancer), endocrine cancer (including, but not imited to, thyroid cancer, and adrenal gland cancer), eye cancer (including, but not limited to, retinoblastoma), female genitourinary cancer (including, but not limited to, cancer of the placenta, uterus, vulva, ovary, cervix), head and neck cancer (including, but not limited to, cancer of the pharynx, oesophagus, and tongue), liver cancer, lung cancer (including, but not limited to, non-small cell lung cancer (NSCLC), small cell lung cancer (SCLC), mucoepidermoid, bronchogenic, squamous cell carcinoma (SQCC), and anaplastic/NSCLC), skin cancer (including, but not limited to, melanoma, and SQCC), soft tissue cancer (including but not limited to, sarcoma, Ewing's sarcoma, and rhabdomyosarcoma), bone cancer (including, but not limited to, sarcoma, Ewing's sarcoma, and osteosarcoma), squamous cell cancer (including, but not limited to, lung, esophageal, cervical, and head and neck cancer), pancreas cancer, kidney cancer (including, but not limited to, renal Wilm's tumor and renal cell carcinoma), and prostate cancer. In one embodiment, the solid tumor is not triple negative breast cancer (TNBC). In some embodiments, the solid tumor is breast cancer, colon cancer, lung cancer or bladder cancer. In one such embodiment, the solid tumor is superficial bladder cancer. In another, the solid tumor is lung squamous cell carcinoma. In yet another embodiment, the solid tumor is luminal B type breast cancer.

As used herein "hematological cancer" includes, but is not limited to, leukemia (including, but not limited to, acute lymphocytic leukemia (ALL), chronic myeloid leukemia (CML), acute T-cell leukemia, B cell precursor leukemia, acute promyelocytic leukemia (APML), plasma cell leukemia, myelomonoblastic/T-ALL, B myelomonocytic leukemia, erythroleukemia, and acute myeloid leukemia (AML)), lymphoma (including but not limited to Hodgkin's lymphoma, non-Hodgkin's lymphoma (NHL), Burkitt's lymphoma (BL), B cell lymphoma, lymphoblastic lymphoma, follicular lymphoma (FL), diffuse large B-cell lymphoma (DLBCL), large cell immunoblastic lymphoma), and multiple myeloma.

In a specific embodiment, provided herein are methods for treating or preventing cancer, comprising administering to a patient having cancer, or to a patient at risk of developing cancer, a pharmaceutically effective amount of ADPR, or a pharmaceutically acceptable salt, solvate, hydrate, tautomer, stereoisomer, isotopologue, pro-drug, or polymorph thereof, wherein the cancer is lung cancer, adenocarcinoma of the lung, non-small cell lung carcinoma, pancreatic cancer, pancreatic adenocarcinoma, glioma, glioblastoma multiforme, or acute myeloid leukemia. In a specific embodiment, the ADPR is in the form of its dilithium salt.

In certain embodiments, provided herein are methods for increasing the amount of free ADPR or ATP in an ADPR or ATP deficient cell in a state of high cytotoxic stress, comprising contacting said cell with an amount of ADPR sufficient to restore normal physiological cellular ADPR or ATP levels.

In one embodiment, the administering step comprises administering ADPR and a metal salt, wherein the total amount of ADPR and the metal salt is in the range of about 0.001 mg to about 5 mg per dose. In one embodiment, each dose is between 10 microliters to 200 microliters. In another embodiment, each dose is between 20 microliters to 80 microliters.

In one embodiment, the administering step comprises administering the pharmaceutical composition in the form of a solution. In one embodiment, the solution is administered to the eye one to eight times a day. In one embodiment, the solution is administered to the eye one to twenty-four times a day.

In one embodiment, the method further comprises the step of storing the composition for at least one month, at least three months, at least six months, or at least 1 year before the administering step.

All compounds described herein are contemplated to be used in the methods described herein and especially in the prevention or treatment of adenovirus-related diseases or conditions, eye disorders, cancer, or diseases or conditions caused by infection, inflammation, or physical, chemical, thermal, or radiation injuries.

5.4 Combination Therapy

In certain embodiments, ADPR or a pharmaceutically acceptable salt, solvate, hydrate, tautomer, stereoisomer, isotopologue, pro-drug, or polymorph thereof, or a pharmaceutical composition thereof, may be administered in combination with another medicament. Such combination therapy may be achieved by way of the simultaneous, sequential, or separate dosing of the individual components of the treatment. Additionally, when administered as a component of such combination therapy, ADPR as disclosed herein, and the other medicament may be synergistic, such that the daily dose of either or both of the components may be reduced as compared to the dose of either component that would normally be given as a monotherapy. Alternatively, when administered as a component of such combination therapy, ADPR as disclosed herein and the other medicament may be additive, such that the daily dose of each of the components is similar or the same as the dose of either component that would normally be given as a monotherapy.

In certain embodiments, the other medicament is an antiviral compound or a metal salt. In some embodiments, the other medicament is cidofovir, acyclovir, or ganciclovir. In a specific embodiment, the other medicament is cidofovir. In certain embodiments, the other medicament is a lithium, zinc, cobalt, or copper salt. In certain embodiments, the other medicament is selected from the group consisting of lithium benzoate, lithium bromide, lithium chloride, lithium sulfate, lithium tetraborate, lithium acetate, zinc chloride, zinc sulfate, zinc bromide, cobalt chloride, cobalt bromide, copper bromide (CuBr$_2$), copper chloride (CuCl$_2$), and copper sulfate. In a specific embodiment, the other medicament is lithium chloride.

In one embodiment, when ADPR is used in combination with cidofovir, the concentration of cidofovir is in the range of about 0.01% to about 0.2%. In some embodiments, the concentration of cidofovir is in the range of about 0.01% to about 0.15%, about 0.01% to about 0.1%, about 0.01% to about 0.05%, about 0.05% to about 0.2%, about 0.05% to about 0.15%, about 0.05% to about 0.1%, about 0.1% to about 0.2%, about 0.1% to about 0.15% or about 0.15% to about 0.2%. In a specific embodiment, the concentration of the cidofovir is no more than about 0.1%. In a specific embodiment, the concentration of cidofovir is about 0.2%, about 0.15%, about 0.1%, about 0.05%, about 0.04%, about 0.03%, about 0.02%, or about 0.01%.

In one embodiment, when ADPR is used in combination with cidofovir, the concentration of cidofovir is in the range of about 0.01 mM to about 10 mM. In some embodiments, the concentration of cidofovir is in the range of about 0.01 mM to about 5 mM, about 0.01 mM to about 3 mM, about 0.01 mM to about 1 mM, about 0.01 mM to about 0.5 mM, about 0.01 mM to about 0.1 mM, about 0.01 mM to about 0.05 mM, about 0.01 mM to about 0.03 mM, about 0.01 mM to about 0.02 mM, about 0.05 mM to about 10 mM, about 0.05 mM to about 5 mM, about 0.05 mM to about 3 mM, about 0.05 mM to about 1 mM, about 0.05 mM to about 0.5 mM, about 0.05 mM to about 0.1 mM, about 0.1 mM to about 10 mM, about 0.1 mM to about 5 mM, about 0.1 mM to about 3 mM, about 0.1 mM to about 1 mM, about 0.1 mM to about 0.5 mM, about 0.5 mM to about 10 mM, about 0.5 mM to about 5 mM, about 0.5 mM to about 3 mM, about 0.5 mM to about 1 mM, about 1 mM to about 10 mM, about 1 mM to about 5 mM, about 1 mM to about 3 mM, about 3 mM to about 10 mM, about 3 mM to about 5 mM, about 5 mM to about 10 mM, about 5 mM to about 7 mM, or about 7 mM to about 10 mM. In a specific embodiment, the cidofovir is used in a concentration of about 0.01 mM, about 0.02 mM, about 0.03 mM, about 0.05 mM, about 0.1 mM, about 0.2 mM, about 0.5 mM, about 0.7 mM, about 1 mM, about 1.5 mM, about 2 mM, about 2.5 mM, about 3 mM, about 3.5 mM, about 4 mM, about 4.5 mM, about 5 mM, about 5.5 mM, about 6 mM, about 6.5 mM, about 7 mM, about 7.5 mM, or about 8 mM.

In one embodiment, when ADPR is used in combination with cidofovir, the molar ratio of ADPR:cidofovir is in the range of about 0.1:1 to about 10,000:1. In some embodiments, the molar ratio of ADPR:cidofovir is in the range of about 0.1:1 to about 7,000:1, about 0.1:1 to about 5,000:1, about 0.1:1 to about 3,000:1, about 0.1:1 to about 1,000:1, about 0.5:1 to about 10,000:1, about 0.5:1 to about 7,000:1, about 0.5:1 to about 5,000:1, about 0.5:1 to about 3,000:1, about 0.5:1 to about 1,000:1, about 1:1 to about 10,000:1, about 1:1 to about 7,000:1, about 1:1 to about 5,000:1, about 1:1 to about 3,000:1, about 1:1 to about 1,000:1, about 5:1 to about 10,000:1, about 5:1 to about 7,000:1, about 5:1 to about 5,000:1, about 5:1 to about 3,000:1, about 5:1 to about 1,000:1, about 10:1 to about 10,000:1, about 10:1 to about 7,000:1, about 10:1 to about 5,000:1, about 10:1 to about 3,000:1, or about 10:1 to about 1,000:1.

In one embodiment, the molar ratio of ADPR:cidofovir is in the range of about 0.1:1 to about 1,000:1. In some embodiments, the molar ratio of ADPR:cidofovir is in the range of about 0.1:1 to about 700:1, about 0.1:1 to about 500:1, about 0.1:1 to about 200:1, about 0.1:1 to about 100:1, about 0.1:1 to about 50:1, about 0.1:1 to about 10:1, about 0.1:1 to about 5:1, about 0.1:1 to about 1:1, about 0.1:1 to about 0.5:1, about 0.5:1 to about 1,000:1, about 0.5:1 to about 700:1, about 0.5:1 to about 500:1, about 0.5:1 to about 200:1, about 0.5:1 to about 100:1, about 0.5:1 to about 50:1, about 0.5:1 to about 10:1, about 0.5:1 to about 5:1, about 0.5:1 to about 1:1, about 1:1 to about 1,000:1, about 1:1 to about 700:1, about 1:1 to about 500:1, about 1:1 to about 200:1, about 1:1 to about 100:1, about 1:1 to about 50:1, about 1:1 to about 10:1, about 1:1 to about 5:1, about 5:1 to about 1,000:1, about 5:1 to about 700:1, about 5:1 to about 500:1, about 5:1 to about 200:1, about 5:1 to about 100:1, about 5:1 to about 50:1, about 5:1 to about 10:1, about 10:1 to about 1,000:1, about 10:1 to about 700:1, about 10:1 to about 500:1, about 10:1 to about 200:1, about 10:1 to about 100:1, about 10:1 to about 50:1, about 50:1 to about 1,000:1, about 50:1 to about 700:1, about 50:1 to about 500:1, about 50:1 to about 200:1, about 50:1 to about 100:1, about 100:1 to about 1,000:1, about 100:1 to about 700:1, about 100:1 to about 500:1, about 100:1 to about 200:1, about 200:1 to about 1,000:1, about 200:1 to about 700:1, about 200:1 to about 500:1, about 500:1 to about 1,000:1, about 500:1 to about 700:1, or about 700:1 to about 1,000:1.

In some embodiments, the molar ratio of ADPR:cidofovir is in the range of about 50:1 to about 10,000:1. In some embodiments, the molar ratio of ADPR:cidofovir is in the range of about 50:1 to about 7,000:1, about 50:1 to about 5,000:1, about 50:1 to about 1,000:1, about 50:1 to about 700:1, about 50:1 to about 500:1, about 50:1 to about 200:1, about 50:1 to about 100:1, about 200:1 to about 10,000:1, about 200:1 to about 7,000:1, about 200:1 to about 5,000:1, about 200:1 to about 1,000:1, about 200:1 to about 700:1, about 200:1 to about 500:1, about 500:1 to about 10,000:1, about 500:1 to about 7,000:1, about 500:1 to about 5,000:1, about 500:1 to about 1,000:1, about 500:1 to about 700:1, about 1,000:1 to about 10,000:1, about 1,000:1 to about 7,000:1, about 1,000:1 to about 5,000:1, about 1,000:1 to about 3,000:1, about 2,000:1 to about 10,000:1, about 2,000:1 to about 7,000:1, about 2,000:1 to about 5,000:1, about 2,000:1 to about 3,000:1, about 3,000:1 to about 10,000:1, about 3,000:1 to about 7,000:1, about 3,000:1 to about 5,000:1, about 3,000:1 to about 4,000:1, about 5,000:1 to about 10,000:1, about 5,000:1 to about 7,000:1, about 5,000:1 to about 6,000:1, about 7,000:1 to about 10,000:1. In a specific embodiment, the molar ratio of ADPR:cidofovir is about 0.1:1, about 0.5:1, about 1:1, about 5:1, about 10:1, about 50:1, about 100:1, about 150:1, about 160:1, about 170:1, about 180:1, about 190:1, about 200:1, about 250:1, about 300:1, about 350:1, about 400:1, about 500:1, about 600:1, about 700:1, about 800:1, about 900:1, about 1,000:1, about 2,000:1, about 5,000:1, about 7,000:1, or about 10,000:1.

5.5 Doses and Dosing Regimens

In certain embodiments, an adenovirus-related disease or condition, an eye disorder, cancer, or a diseases or condition caused by infection, inflammation, or physical, chemical, thermal, or radiation injuries as described herein may be treated by administering to a patient having a disease or condition as described herein from about 0.005 mg/kg to about 1000 mg/kg, about 0.01 mg/kg to about 100 mg/kg, about 0.1 mg/kg to about 10 mg/kg or about 0.1 mg/kg to about 5.0 mg/kg of ADPR, or a pharmaceutically acceptable salt, solvate, hydrate, tautomer, stereoisomer, isotopologue, pro-drug, or polymorph thereof.

In certain embodiments, the adenovirus-related disease or condition, an eye disorder, cancer, or a diseases or condition caused by infection, inflammation, or physical, chemical, thermal, or radiation injuries as described herein may be treated by administering to a patient having or at risk of developing a disease or condition as described herein an amount of about 0.005 mg to about 1000 mg, about 0.01 mg to about 100 mg, about 0.01 mg to about 10 mg, about 0.01 mg to about 1 mg, about 0.01 mg to about 0.1 mg, about 0.1 mg to about 10 mg, about 0.1 mg to about 5.0 mg, 0.1 mg to about 1 mg of ADPR, or a pharmaceutically acceptable salt, solvate, hydrate, tautomer, stereoisomer, isotopologue, pro-drug, or polymorph thereof. In one embodiment, the concentration of ADPR, or a pharmaceutically acceptable salt, solvate, hydrate, tautomer, stereoisomer, isotopologue, pro-drug, or polymorph thereof is in the range of about 0.05 mg/mL to about 30 mg/mL. In another embodiment, the concentration of ADPR, or a pharmaceutically acceptable salt, solvate, hydrate, tautomer, stereoisomer, isotopologue, pro-drug, or polymorph thereof is in the range of about 1 mg/mL to about 20 mg/mL. In certain such embodiments, ADPR as described herein is administered by topical, oral, parenteral, mucosal, or inhalation route of administration. In one embodiment, ADPR as described herein is administered by topical administration. In one embodiment, the topical administration is to an interior cellular or tissue surface. In a specific embodiment, the topical administration to an interior cellular or tissue surface is by aerosolization, spray, oral delivery, infusion or similar method to any surface of the respiratory tract. In another specific embodiment, the topical administration to an interior cellular or tissue surface is by oral delivery, infusion, or enema to any surface of the gastrointestinal tract (e.g., from the mouth to the anus). In another specific embodiment, the topical administration to an interior cellular or tissue surface is by parenteral injection or infusion to any internal organ. In another embodiment, the topical administration is to an exterior cellular or tissue surface, including, but not limited to, the skin, eye, nail, hair, or ear. In a specific embodiment, ADPR as described herein is administered topically in a concentration ranging from about 0.05 mg/mL to about 30 mg/mL. In another embodiment, ADPR as described herein is administered topically in a concentration ranging from about 1 mg/mL to about 20 mg/mL.

In certain embodiments, the adenovirus-related disease or condition, an eye disorder, cancer, or a diseases or condition caused by infection, inflammation, or physical, chemical, thermal, or radiation injuries as described herein may be treated by administering to a patient having or at risk of developing a disease or condition as described herein a daily dose of about 0.005 mg to about 1000 mg, about 0.01 mg to about 100 mg, about 0.01 mg to about 10 mg, about 0.01 mg to about 1 mg, about 0.01 mg to about 0.1 mg, about 0.1 mg to about 10 mg, about 0.1 mg to about 5.0 mg, 0.1 mg to about 1 mg of ADPR, or a pharmaceutically acceptable salt, solvate, hydrate, tautomer, stereoisomer, isotopologue, pro-drug, or polymorph thereof. In one embodiment, the concentration of ADPR, or a pharmaceutically acceptable salt, solvate, hydrate, tautomer, stereoisomer, isotopologue, pro-drug, or polymorph thereof is in the range of about 0.05 mg/mL to about 30 mg/mL. In another embodiment, the concentration of ADPR, or a pharmaceutically acceptable salt, solvate, hydrate, tautomer, stereoisomer, isotopologue, pro-drug, or polymorph thereof is in the range of about 1 mg/mL to about 20 mg/mL. In certain such embodiments, ADPR as described herein is administered by topical, oral, parenteral, mucosal, or inhalation route of administration. In one embodiment, ADPR as described herein is administered by topical administration. In one embodiment, the topical administration is to an interior cellular or tissue surface. In a specific embodiment, the topical administration to an interior cellular or tissue surface is by aerosolization, spray, oral delivery, infusion or similar method to any surface of the respiratory tract. In another specific embodiment, the topical administration to an interior cellular or tissue surface is by oral delivery, infusion, or enema to any surface of the gastrointestinal tract (e.g., from the mouth to the anus). In another specific embodiment, the topical administration to an interior cellular or tissue surface is by parenteral injection or infusion to any internal organ. In another embodiment, the topical administration is to an exterior cellular or tissue surface, including, but not limited to, the skin, eye, nail, hair, or ear. In a specific embodiment, ADPR as described herein is administered topically in a concentration ranging from about 0.05 mg/mL to about 30 mg/mL. In another embodiment, ADPR as described herein is administered topically in a concentration ranging from about 1 mg/mL to about 20 mg/mL.

The suitability of ADPR, or a pharmaceutically acceptable salt, solvate, hydrate, tautomer, stereoisomer, isotopologue, pro-drug, or polymorph thereof, for the treatment or prevention of an adenovirus-related disease or condition, an eye disorder, cancer, or a diseases or condition caused by infection, inflammation, or physical, chemical, thermal, or radiation injuries as described herein can be confirmed by using the assays described herein. For example, adenovirus can be diagnosed by viral culture, polymerase chain reaction, or by rapid test such as Adenoplus® or similar technology from bodily fluids (sputum, tears, or other fluids sampled by swab or similar technique).

5.6 Pharmaceutical Compositions

Pharmaceutical compositions may be used in the preparation of individual, single unit dosage forms. Pharmaceutical compositions and dosage forms of the present invention comprise ADPR, or a pharmaceutically acceptable salt, solvate, hydrate, tautomer, stereoisomer, isotopologue, pro-drug, or polymorph thereof. The pharmaceutical compositions and dosage forms of the present invention can be prepared by any known or otherwise effective method for formulating or manufacturing the selected product form. For example, ADPR, or a pharmaceutically acceptable salt, solvate, hydrate, tautomer, stereoisomer, isotopologue, pro-drug, or polymorph thereof, can be formulated along with common excipients, diluents, or carriers, and formed into tablets, capsules, solutions, suspensions, emulsions, microemulsions, nanoemulsions, syrups, elixirs, sprays, powders, aerosols (e.g., dry powder aerosols, liquid aerosols), dissolving media (e.g., rapid dissolving tablet, film, strip), suppositories, ointments, or any other suitable dosage form. In a specific embodiment, the pharmaceutical composition is in the form of a solution.

Non-limiting examples of suitable excipients, diluents, and carriers include: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as acetyl alcohol, glycerol monostearate; adsorptive carriers such as kaolin and bentonite; carriers such as propylene glycol and ethyl alcohol, and lubricants such as talc, calcium and magnesium stearate, and solid polyethyl glycols.

Like the amounts and types of excipients, the amount and specific type of the active ingredient (e.g., ADPR as disclosed herein) in a dosage form may differ depending on factors including, but not limited to, the route by which it is to be administered to patients. In certain embodiments, administration of the pharmaceutical composition or dosage form comprising ADPR, or a pharmaceutically acceptable salt, solvate, hydrate, tautomer, stereoisomer, isotopologue, pro-drug, or polymorph thereof, may be by topical, oral, parenteral, mucosal, or inhalation route. As used herein, the term "parenteral" includes intravitreous, intraocular, intracorneal, subcutaneous, intradermal, intravascular injections, such as intravenous, intra-arterial, intramuscular, intraluminal and any another similar injection or infusion technique. In certain embodiments, ADPR, or a pharmaceutically acceptable salt, solvate, hydrate, tautomer, stereoisomer, isotopologue, pro-drug, or polymorph thereof, may be administered orally, such as in a tablet, capsule, or liquid formulation. In certain embodiments, ADPR, or a pharmaceutically acceptable salt, solvate, hydrate, tautomer, stereoisomer, isotopologue, pro-drug, or polymorph thereof, may be administered topically. In certain embodiments, ADPR, or a pharmaceutically acceptable salt, solvate, hydrate, tautomer, stereoisomer, isotopologue, pro-drug, or polymorph thereof, may be administered intranasally or by inhalation.

Topical administration as described herein includes applying a pharmaceutically effective amount of ADPR, or a pharmaceutically acceptable salt, solvate, hydrate, tautomer, stereoisomer, isotopologue, pro-drug, or polymorph thereof, to any mucosal and/or epithelial surface of the body including that associated with, but not limited to, the skin, eyes, ears, nose, sinuses, mouth, lips, pharynx, larynx, epiglottis, trachea, bronchi, bronchioles, alveoli, esophagus, stomach, intestines, colon, rectum, anus, vagina, cervix, and any other portions of the dermatologic, gastrointestinal, respiratory, and/or genitourinary tracts. In another embodiment, topical administration as described herein includes applying a pharmaceutically effective amount of ADPR, or a pharmaceutically acceptable salt, solvate, hydrate, tautomer, stereoisomer, isotopologue, pro-drug, or polymorph thereof, to any wound due to injury, surgery, infection, inflammation, or cancer.

Additionally, ADPR, or a pharmaceutically acceptable salt, solvate, hydrate, tautomer, stereoisomer, isotopologue, pro-drug, or polymorph thereof, can also be formulated as a sustained or prolonged release dosage forms including a dosage form that releases the active ingredient only or preferably in a particular part of the intestinal tract, preferably over an extended or prolonged period of time to further enhance effectiveness. In one embodiment, ADPR as described herein is formulated as a sustained or prolonged release dosage form including a dosage form that releases the active ingredient only or preferably in a particular part of the respiratory tract, preferably over an extended or prolonged period of time to further enhance effectiveness. The coatings, envelopes, and protective matrices in such a dosage form may be made, for example, from polymeric substances or waxes well known in the pharmaceutical arts.

In one embodiment, provided herein are pharmaceutical compositions comprising ADPR, wherein the amount of ADPR in the pharmaceutical composition is in the range of about 0.001% w/w to about 10% w/w of the pharmaceutical composition. In one embodiment, the amount of ADPR in the pharmaceutical composition is in the range of about 0.001% w/w to about 7% w/w, about 0.001% w/w to about 5% w/w, about 0.001% w/w to about 3% w/w, about 0.001% w/w to about 1% w/w, about 0.001% w/w to about 0.5% w/w, about 0.001% w/w to about 0.1% w/w, about 0.001% w/w to about 0.05% w/w, about 0.001% w/w to about 0.01% w/w, about 0.001% w/w to about 0.005% w/w, about 0.005% w/w to about 10% w/w, about 0.005% w/w to about 7% w/w, about 0.005% w/w to about 5% w/w, about 0.005% w/w to about 3% w/w, about 0.005% w/w to about 1% w/w, about 0.005% w/w to about 0.5% w/w, about 0.005% w/w to about 0.1% w/w, about 0.005% w/w to about 0.05% w/w, about 0.005% w/w to about 0.01% w/w, about 0.01% w/w to about 10% w/w, about 0.01% w/w to about 7% w/w, about 0.01% w/w to about 5% w/w, about 0.01% w/w to about 3% w/w, about 0.01% w/w to about 1% w/w, about 0.01% w/w to about 0.5% w/w, about 0.01% w/w to about 0.1% w/w, about 0.01% w/w to about 0.05% w/w, about 0.05% w/w to about 10% w/w, about 0.05% w/w to about 7% w/w, about 0.05% w/w to about 5% w/w, about 0.05% w/w to about 3% w/w, about 0.05% w/w to about 1% w/w, about 0.05% w/w to about 0.5% w/w, about 0.05% w/w to about 0.1% w/w, about 0.1% w/w to about 10% w/w, about 0.1% w/w to about 7% w/w, about 0.1% w/w to about 5% w/w, about 0.1% w/w to about 3% w/w, about 0.1% w/w to about 1% w/w, about 0.1% w/w to about 0.5% w/w, about 0. 5% w/w to about 10% w/w, about 0. 5% w/w to about 7% w/w, about 0. 5% w/w to about 5% w/w, about 0. 5% w/w to about 3% w/w, about 0.5% w/w to about 1% w/w, about 1% w/w to about 10% w/w, about 1% w/w to about 7% w/w, about 1% w/w to about 5% w/w, about 1% w/w to about 3% w/w, about 3% w/w to about 10% w/w, about 3% w/w to about 7% w/w, about 3% w/w to about 5% w/w, about 5% w/w to about 10% w/w, about 5% w/w to about 7% w/w, or about 7% w/w to about 10% w/w of the pharmaceutical composition.

In one embodiment, the amount of ADPR in the pharmaceutical composition is in the range of about 0.01% w/w to about 10% w/w of the pharmaceutical composition. In one embodiment, the amount of ADPR in the pharmaceutical composition is in the range of about 0.1% w/w to about 2.5% w/w of the pharmaceutical composition. In another embodiment, the amount of ADPR in the pharmaceutical composition is in the range of about 0.5% w/w to about 2% w/w of the pharmaceutical composition.

In one embodiment, provided herein is a pharmaceutical composition suitable for topical administration to the eye, respiratory tract, and/or gastrointestinal tract effective for treatment and/or prophylaxis of a microorganism infection or a disorder of at least one tissue of the eye, respiratory tract, and/or gastrointestinal tract, wherein the pharmaceutical composition comprises ADPR, wherein the amount of ADPR is in the range of about 0.01% w/w to about 10% w/w of the pharmaceutical composition.

In one embodiment, provided herein is a pharmaceutical composition suitable for topical administration to the eye, respiratory tract, and/or gastrointestinal tract, effective for treatment and/or prophylaxis of a microorganism infection or a disorder of at least one tissue of the eye, respiratory tract, or gastrointestinal tract, wherein the pharmaceutical composition comprises: a) ADPR, wherein the amount of ADPR is in the range of about 0.01% w/w to about 10% w/w of the pharmaceutical composition; and b) one or more metal salts, wherein the metal is selected from the group consisting of lithium, zinc, cobalt, and copper. In one embodiment, the amount of the metal salt in the pharmaceutical composition is in the range of about 0.0001% w/w to about 2% w/w of the pharmaceutical composition. In another embodiment, the amount of the metal salt in the pharmaceutical composition is the range of about 0.01% w/w to about 1% w/w of the pharmaceutical composition.

In one embodiment, the microorganism is selected from the group consisting of bacteria, viruses, fungi, and amoebae. In one embodiment, the bacteria is mycobacteria. In one embodiment, the prophylaxis is prophylaxis of infection following corneal abrasion or ocular surgery.

In one embodiment, the pharmaceutical composition is suitable for administration to the eye. In a specific embodiment, the pharmaceutical composition suitable for administration to the eye further comprises a topical anesthetic which relieves pain. In one embodiment, the topical anesthetic is selected from the group consisting of proparacaine, lidocaine, tetracaine and combinations thereof.

In one embodiment, the pharmaceutical composition further comprises a penetration enhancer which enhances the penetration of ADPR into the tissues of the eye, respiratory tract, or gastrointestinal tract. In a specific embodiment, the penetration enhancer is a topical anesthetic.

In one embodiment, the pharmaceutical composition further comprises an antimicrobial preservative. In one embodiment, the antimicrobial preservative is selected from the group consisting of sodium tetraborate, boric acid, benzalkonium chloride, thimerosal, chlorobutanol, methyl paraben, propyl paraben, phenylethyl alcohol, EDTA, sorbic acid, Onamer M and combinations thereof. In one embodiment, the amount of antimicrobial preservative in the pharmaceutical composition is in the range of about 0.001% w/w to about 1.0% w/w by weight of the pharmaceutical composition. In a specific embodiment, the pharmaceutical composition is in the form of a solution.

In one embodiment, the pharmaceutical composition further comprises a cosolvent/surfactant. In one embodiment, the cosolvent/surfactant is selected from the group consisting of polysorbate 20, polysorbate 60, polysorbate 80, Pluronic F68, Pluronic F84, Pluronic P103, cyclodextrin, tyloxapol and combinations thereof. In one embodiment, the amount of the cosolvent/surfactant in the pharmaceutical composition is in the range of about 0.01% w/w to about 2% w/w of the pharmaceutical composition.

In one embodiment, the pharmaceutical composition further comprises one or more viscosity increasing agents. In one embodiment, the viscosity increasing agent is selected from the group consisting of polyvinyl alcohol, polyvinyl pyrrolidone, methyl cellulose, hydroxy propyl methylcellulose, hydroxyethyl cellulose, carboxymethyl cellulose, hydroxy propyl cellulose, polyethylene glycol, and combinations thereof. In one embodiment, the amount of the viscosity increasing agent in the pharmaceutical composition is in the range of about 0.01% w/w to about 2% w/w of the pharmaceutical composition. In a specific embodiment, the pharmaceutical composition is in the form of a solution.

In one embodiment, the pharmaceutical composition is in the form of a solution, suspension, emulsion, ointment, cream, gel, or a controlled release/sustained release formulation. In one embodiment, the pharmaceutical composition is in the form of an aqueous solution.

5.6.1 Topical Ocular Formulations

In certain embodiments, a pharmaceutical formulation described in above may be specifically adjusted for topical application to the eye. In certain specific embodiments, disclosed herein are pharmaceutical formulations comprising ADPR as described herein as topical ophthalmic solutions or suspensions (eye drops), which are normally available as a sterile, isotonic (i.e., a pH of between about 3 and about 8, between about 4 to about 8, between about 7 to about 8, or about 7.4) solution, optionally further comprising a preservative and/or a viscosity enhancer.

The term "eye drops" as used herein refers to a pharmaceutical liquid formulation which is administered in the form of drops on the external surface of the eye and which has a local effect on the posterior segment of the eye, including the choroids, retinal pigment epithelium, retina, macula, fovea, optic nerve and vitreous humor.

Accordingly, in certain embodiments, a pharmaceutical formulation provided herein comprising ADPR as described herein, may be formulated with purified water and adjusted for physiological pH and isotonicity. Examples of buffering agents to maintain or adjust pH include, but are not limited to, acetate buffers, citrate buffers, phosphate buffers and borate buffers. Examples of tonicity adjustors are sodium chloride, mannitol and glycerin.

The eye drop formulation is then optionally aliquoted into either a plurality of discrete, sterile disposable cartridges each of which is suitable for unit dosing, or a single cartridge for unit dosing. Such a single disposable cartridge may be, for example, a conical or cylindrical specific volume dispenser, with a container having side-walls squeezable in a radial direction to a longitudinal axis in order to dispense the container contents therefrom at one end of the container. Such disposable containers can be used to dispense eye drops at 0.3 to 0.4 mL per unit dosing, and are ideally adaptable for the delivery of eye drops.

Ophthalmic eye-drop solutions or suspensions may also be packaged in multi-dose form, for example, as a plastic bottle with an eye-dropper. In such formulations, preservatives are optionally added to prevent microbial contamination after opening of the container. Suitable preservatives include, but are not limited to: sodium tetraborate, boric acid, benzalkonium chloride, thimerosal, chlorobutanol, methylparaben, propylparaben, phenylethyl alcohol, edetate disodium, sorbic acid, polyquaternium-1, or other agents known to those skilled in the art, and all of which are contemplated for use in the present invention. Preservative-containing formulations may comprise from about 0.001 to about 1.0% weight/volume of the preservative.

In certain embodiments, polymers may be added to ophthalmic solutions or suspensions in order to increase the viscosity of the vehicle, thereby prolonging contact of the solution or suspension with the cornea and enhancing bioavailability. In certain embodiments, such polymers are selected from cellulose derivatives (e.g., methylcellulose, hydroxyethylcellulose, hydroxypropylcellulose or carboxymethylcellulose), dextran 70, gelatin, polyols, glycerin, polyethylene glycol 300, polyethylene glycol 400, polysorbate 80, propylene glycol, polyvinyl alcohol and povidone, or a combination thereof.

In certain embodiments ophthalmic solutions or suspensions as disclosed herein may further comprise stabilizer/solubilizer such as a cyclodextrin. In certain such embodiments, the cyclodextrin is selected from α-cyclodextrin, β-cyclodextrin, γ-cyclodextrin, hydroxypropyl-β-cyclodextrin, hydroxypropyl-γ-cyclodextrin, dimethyl-β-cyclodextrin and dimethyl-γ-cyclodextrin.

In certain embodiments, a pharmaceutical formulation as disclosed herein, such as a pharmaceutical formulation comprising ADPR as described herein, may be administered in a sustained release ophthalmic solution or suspension formulation.

In certain embodiments, a pharmaceutical formulation as disclosed herein, such as a pharmaceutical formulation comprising ADPR as described herein, may be formulated for administration through an ocular drug delivery system, such as, but not limited to, a colloidal dosage form, such as nanoparticles, nanomicelles, liposomes, microemulsions, bioadhesive gels and fibrin sealant-based approaches to sustain drug levels at the target site. Other ocular drug delivery systems include drug-eluting contact lenses, ultrasound-mediated drug delivery, ocular iontophoresis, and drug-coated microneedles.

In certain embodiments, the frequency of administration can vary greatly. Depending on the needs of each subject and the severity of the disease to be treated, such administration may occur once every 6 months, once every 5 months, once every 4 months, once every 3 months, once every 2 months, once a month, once every 3 weeks, once every 2 weeks, once a week, once every 6 days, once every 5 days once every 4 days once every 3 days, once every 2 days, or once a day.

In certain embodiments, the frequency of administration can vary greatly, depending on the needs of each subject and the severity of the disease to be treated, such administration may be from about once a week to about ten times a day, such as from about three times a week to about three times a day, or once or twice a day.

In one embodiment, provided herein is an ophthalmic composition suitable for topical administration to an eye, effective for treatment and/or prophylaxis of a microorganism infection or a disorder of at least one tissue of the eye, wherein the ophthalmic composition comprises: a) ADPR, wherein the amount of ADPR is in the range of about 0.01% w/w to about 10% w/w of the ophthalmic composition, and b) cidofovir. In one embodiment, the ophthalmic composition comprises: a) ADPR, wherein the amount of ADPR is in the range of about 0.3% w/w to about 3% w/w of the ophthalmic composition; and b) cidofovir, wherein the amount of cidofovir is in the range of about 0.05% w/w to about 2% w/w of the ophthalmic composition.

5.6.2 Formulations for Intranasal Administration or by Inhalation

In certain embodiments, the pharmaceutical composition provided herein is administered intranasally or by inhalation to the respiratory tract. The pharmaceutical composition can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical composition can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical composition provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as 1-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

5.6.3 Oral Formulations

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art.

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105

(available from FMC Corporation, American Viscose Division, Avicel Sales, Marcus Hook, PA), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM. Other suitable forms of microcrystalline cellulose include, but are not limited to, silicified microcrystalline cellulose, such as the materials sold as PROSOLV 50, PROSOLV 90, PROSOLV HiD90, PROSOLV 90 LM, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

In certain embodiments, fillers may include, but are not limited to block copolymers of ethylene oxide and propylene oxide. Such block copolymers may be sold as POLOXAMER or PLURONIC, and include, but are not limited to POLOXAMER 188 NF, POLOXAMER 237 NF, POLOXAMER 338 NF, POLOXAMER 437 NF, and mixtures thereof.

In certain embodiments, fillers may include, but are not limited to isomalt, lactose, lactitol, mannitol, sorbitol xylitol, erythritol, and mixtures thereof.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, povidone, crospovidone, polacrilin potassium, sodium starch glycolate, potato or tapioca starch, other starches, pre-gelatinized starch, other starches, clays, other algins, other celluloses, gums, and mixtures thereof.

Glidants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium stearyl fumarate, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional glidants include, for example, a syloid silica gel (AEROSIL200, manufactured by W.R. Grace Co. of Baltimore, MD), a coagulated aerosol of synthetic silica (marketed by Degussa Co. of Plano, TX), CAB-O-SIL (a pyrogenic colloidal silicon dioxide product sold by Cabot Co. of Boston, MA), and mixtures thereof. If used at all, glidants may be used in an amount of less than about 1 weight percent of the pharmaceutical compositions or dosage forms into which they are incorporated.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

6 EXAMPLES

6.1 Example 1. Plaque Inhibition Testing of Two (2) Compounds Against Adenovirus Serotype 3

Background

Adenosine 5'-diphosphoribose Sodium Salt ("Compound A" or ADPR, Sigma A0752-500 mg, Lot SLBJ4805V, in one 500 mg vial), and Nicotinamide ("Compound N," Sigma N0636-100G, Lot SLB0315V, in one 100 gm vial) ("Compound N") were obtained from Sigma. Compound A was solubilized to 120 mg/ml in water for irrigation then further to target concentrations 6 mg/ml and 2 mg/ml in DMEM (Dulbecco's Modified Eagle Medium), 2% FBS (Fetal Bovine Serum; virus growth media). A volume of 10 ml of a 240 mg/ml solution of Compound N was made in water for irrigation. Further dilutions of Compound N were made in DMEM, 2% FBS. Adenovirus plaque inhibition assays were set up on the same day. The remainder of the solubilized Compound A was placed at 4° C. in the dark.

Dilutions

Solubilized Compound A was diluted 1:20 or 1:60 in virus growth media to make Sample dilutions of 6 mg/ml and 2 mg/ml respectively. Dilutions of Compound N were made into solutions already containing Compound A. The design of the experiment with Groups 1 to 5 is outlined in text below and presented in Table 1. Groups 2, 3 and 4 consist of mixtures of various concentration samples "Samples" of Compound A and Compound N. Group 4 also contains various amounts of cidofovir, an adenoviral antiviral.

Group 1: Compound N at 0, 60, 600, and 6000 mcg/mL

Group 2: Compound A at 2000 mcg/mL with Compound N at 0, 60, 600, and 6000 mcg/mL Group 3: Compound A (as in the first study) at 6000 mcg/mL with Compound N at 0, 60, 600, and 6000 mcg/mL Group 4: Compound A (as in the first study) at 2000 mcg/mL, Cidofovir at 20 micromolar, with Compound N at 0, 60, 600, and 6000 mcg/mL Group 5: Cidofovir at 0, 20, and 100 micromolar Approach A549 cells were plated $7 \times 10^4$ cells per well in 6-well plates. After 18 hours growth media was removed and 1 ml of each Sample mixtures was added. After incubating one hour at 37° C., approximately 50-75 plaque forming units influenza virus Ad3 were added per well.

Virus was permitted to adsorb to the cells for two hours and then the media was aspirated from the monolayers and replaced with Ad3 growth media containing Sample dilutions per Table 1, and agarose.

Toxicity

Toxicity was evaluated against the below criteria and used to assess the effects of the dilutions of Sample on cell monolayers at the termination of the assay on the end day. Values are recorded in Table 1 as a T value.
 0—No Cytotoxicity
 1—Slight Thinning of Cells compared to Cell Control wells
 2—Moderate thinning of cells compared to Cell Control wells, moderately less intense staining of cells compared to Cell control wells, viral plaques are visible
 3—Extreme thinning of cells compared to Cell Control wells to no cells present, extremely less intense staining of cells compared to Cell Control wells to no staining due to lack of cells, viral plaques are not visible.

Results

Figure 1:
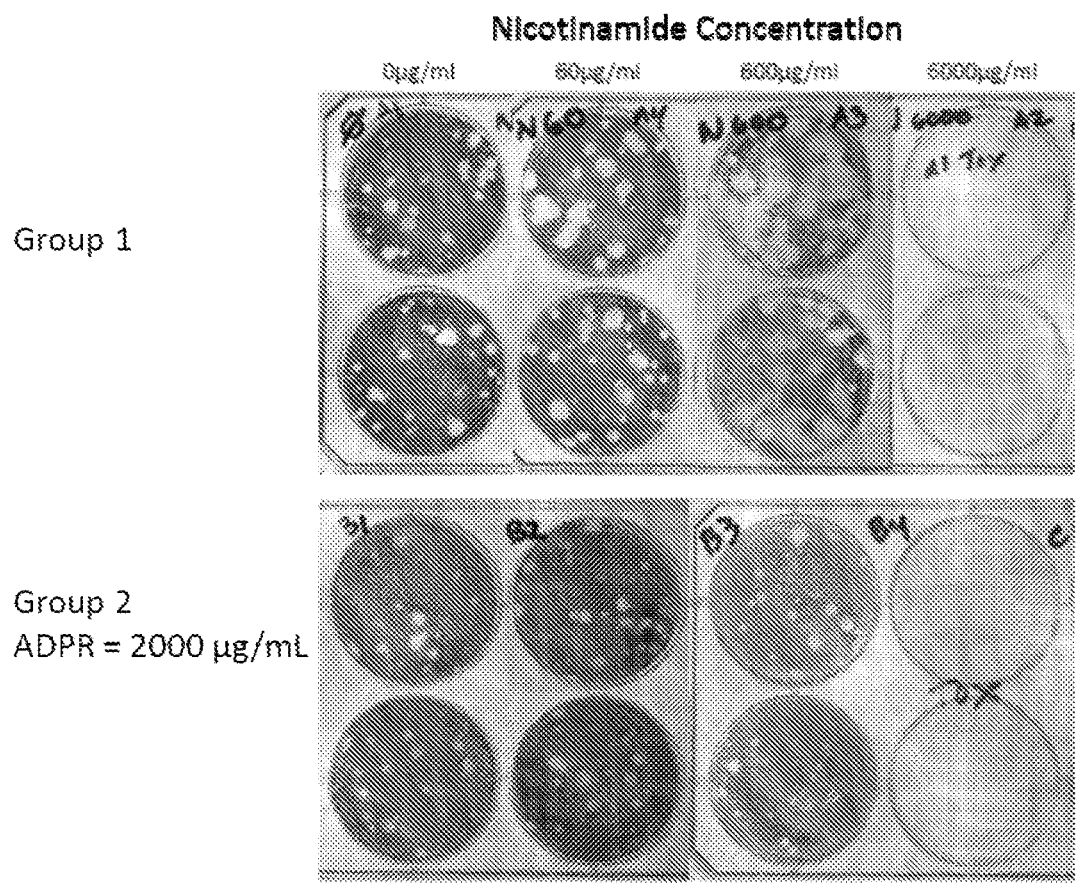
FIG. 1 shows plaque formation from adenovirus serotype 3 in A549 cells and the effects of different concentrations of ADPR (monosodium salt), nicotinamide, cidofovir, and combinations thereof.
Figure 1:
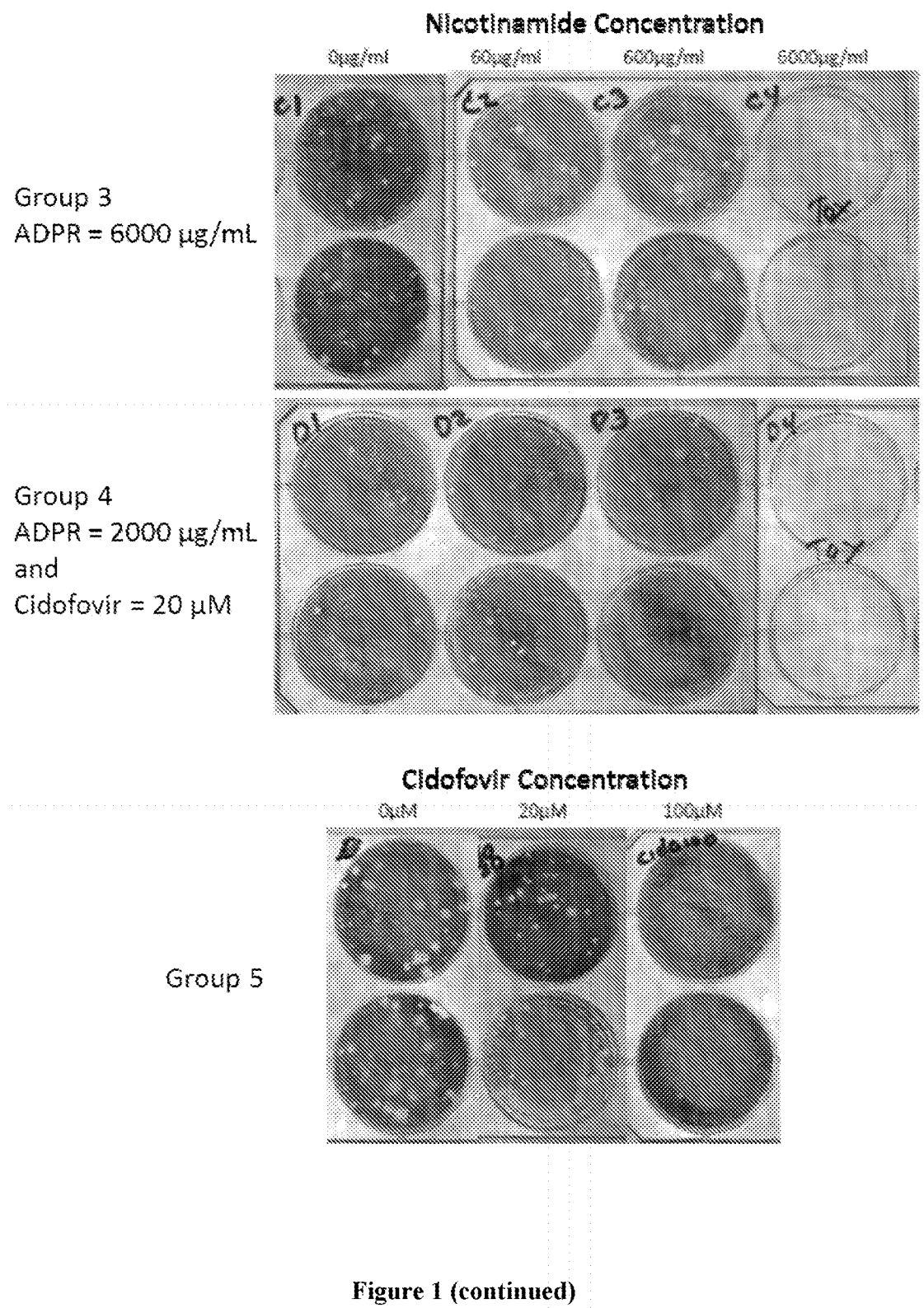
Figure 2:
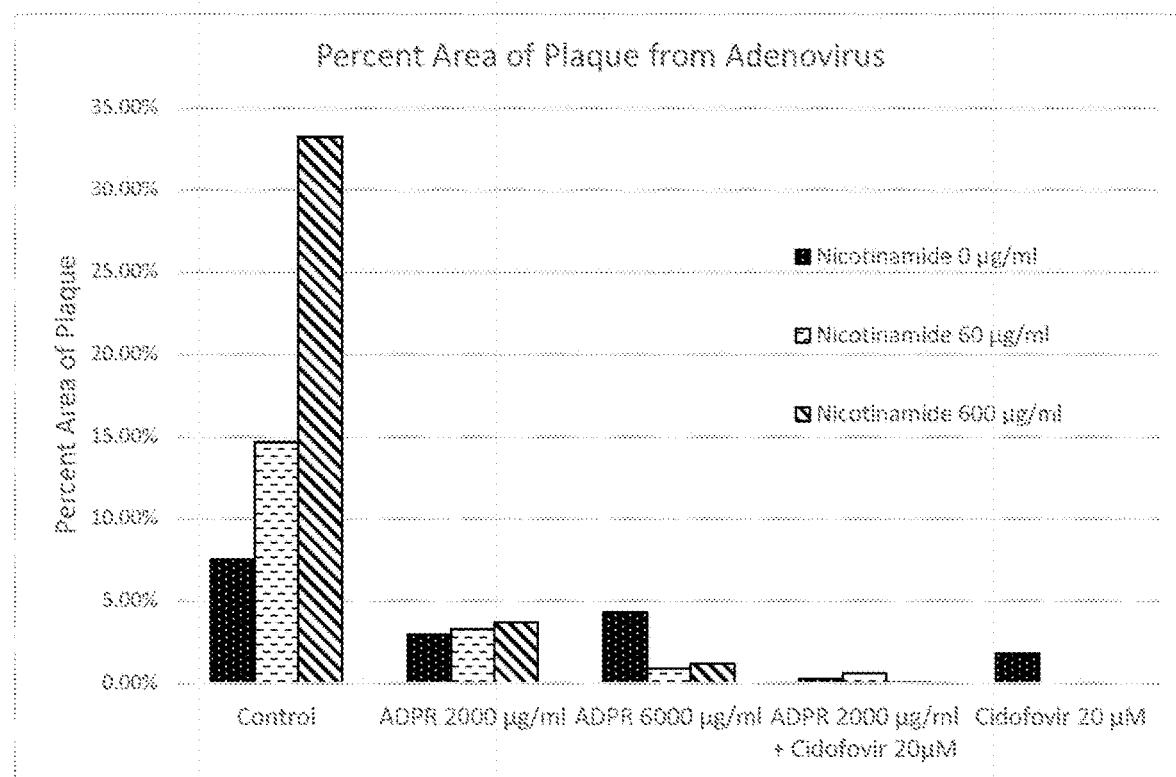
FIG. 2 is a graph depicting the effect of ADPR (monosodium salt) on plaque formation in A549 cells, utilizing an adenovirus plaque inhibition assay. Specifically.

Plaque size was reduced with the treatment of Compound A at 2000 and 6000 µg/ml as compared to control, see plaque counts in Table 1 and FIG. 1. Additions of increasing concentrations of nicotinamide had an additional effect of decreasing the number of discernable plaques. A concentration of 6000 µg/ml nicotinamide was toxic to A549 cell monolayers in all Groups. At 600 µg/ml concentration nicotinamide alone, the adenovirus plaques appeared much larger, possibly because of its effect on the cell monolayer. When 600 µg/ml nicotinamide was mixed with Compound A in Group 2 and Group 3, there was a decrease in the number of discernable plaques. The addition of 20 µM cidofovir was additionally inhibitory in Group 4, and had a synergistic effect compared to Group 3. These results were confirmed by routine image analysis to determine percent plaque area (see FIG. 2). Image analysis was performed with Adobe Photoshop. To perform this analysis, contrast was adjusted equally across plates in order to better identify the plaque formations. A standard circular area of 78,456 pixels per plate was selected at the center of each plate to avoid edge artifacts related to the cell culture. The 'Color Range' function was then used to identify the number of white pixels within the circular area and then divided by the total pixel area to compute the percent plaque area. Results were analyzed in Microsoft Excel 2016. Values for duplicate plates were averaged. The synergistic inhibitory effect for cidofovir (20 µM) with ADPR (2000 µg/ml) was confirmed in the image analysis (FIG. 2) such that the combination had a nearly three-fold benefit (observed 0.25% vs. expected 0.69%) over the expected effect if the compounds were just additive.

TABLE 1

Plaque Counts, Toxicity Scores and Plate codes

| | Group | 0 µg/ml Compound N | 60 µg/ml Compound N | 600 µg/ml Compound N | 6000 µg/ml Compound N |
|---|---|---|---|---|---|
| 1 | 0 µg/ml Compound A | 38, 49<br>T = 0<br>Plate code A1 | 40, 43<br>T = 0<br>Plate code A4 | 38, 45<br>T = 2<br>Plate code A3 | Toxic<br>T = 3<br>Plate code A2 |
| 2 | 2000 µg/ml Compound A | 33, 39<br>T = 0<br>Plate code B1 | 43, 40<br>T = 0<br>Plate code B2 | 22, 26<br>T = 1<br>Plate code B3 | Toxic<br>T = 3<br>Plate code B4 |
| 3 | 6000 µg/ml Compound A | 47, 30<br>T = 0<br>Plate code C1 | 24, 22<br>T = 1<br>Plate code C2 | 22, 24<br>T = 1<br>Plate code C3 | Toxic<br>T = 3<br>Plate code C4 |
| 4 | 2000 µg/ml Compound A + 20 µM Cidofovir | 13, 14<br>T = 1<br>Plate code D1 | 19, 23<br>T = 1<br>Plate code D2 | 8, 7<br>T = 1<br>Plate code D3 | Toxic<br>T = 1<br>Plate code D4 |
| 5 | Controls | No drug<br>51, 47 | 20 µM Cidofovir<br>39 | 100 µM Cidofovir<br>20, 24 pinpoint | |

Control Drug

Cidofovir is known to decrease adenovirus plaque size and was used in concentrations per Table 1. Cidofovir decreased plaques size and number as concentrations were increased.

Raw Materials

TABLE 2

Raw Materials

| | |
|---|---|
| 1. | HyClone DMEM/High Glucose media, Catalog Nr. SH30022.01, Lot AZK194774 |
| 2. | Seradign Fetal Calf Serum, PN 1400-500, Lot 081A11 |
| 3. | Mediatech Trypsin EDTA, 1X, Catalog Nr. 25052-CV, Lot 25052422 |
| 4. | Mediatech Antibiotic Antimycotic Solution, Catalog Nr. 30-004-CI, Lot 30004115 |
| 5. | Adenovirus 3, VIRAPUR Lot A125B |
| 6. | A549 Cells for Adenovirus, batch 1-26-2015 |

6.2 Example 2. Plaque Inhibition of Adenovirus Serotype 3 by ADPR and Lithium Chloride Background Adenosine 5'-diphosphoribose Sodium Salt ("Sample A" or ADPR, Sigma A0752-500 mg, Lot SLBJ4805V, in one 500 mg vial), and Lithium Chloride ("Sample L," Amresco 0416-100 g, Lot 3005C057, in one 100 gm vial) were received as powder and stored until use. On the day of the assay, Sample A was solubilized to 120 mg/ml (200 mM) in water for irrigation then further to target concentrations 4 mM, 1.33 mM and 0.44 mM in Virus Growth Media (DMEM, 2% Fetal Bovine Serum (FBS) and antibiotic, antimycotic). A 200 mM solution of Sample L was made in water for irrigation. Further dilutions of Sample L were made in Virus Growth Medium to achieve desired concentrations in Table 3. The remainder of the solubilized Sample A was placed at 4° C. in the dark.

Dilutions

Solubilized Sample A and Sample L were diluted 1:50, 1:150 and 1:450 in Virus Growth Media to make Sample dilutions. Mixtures of Sample A and L were made by diluting stocks into Virus Growth Media.

Approach

A549 cells were plated $7 \times 10^4$ cells per well in 6-well plates. After 18 hours, growth media was removed and 1 ml of each Sample mixtures was added. After incubating one hour at 37° C., approximately 50-75 plaque forming units Ad3 were added per well. Virus was permitted to adsorb to the cells for two hours and then the media was aspirated from the monolayers and replaced with Virus Growth Media containing Sample dilutions per Table 3, and agarose.

Toxicity

Toxicity was evaluated against the below criteria and used to assess effects of the dilutions of Sample on cell monolayers at the termination of the assay on the end day. Values are recorded in Table 3 as a T value.

0—No Cytotoxicity
1—Slight Thinning of Cells compared to Cell Control wells
2—Moderate thinning of cells compared to Cell Control wells, moderately less intense staining of cells compared to Cell control wells, viral plaques are visible
3—Extreme thinning of cells compared to Cell Control wells to no cells present, extremely less intense staining of cells compared to Cell Control wells to no staining due to lack of cells, viral plaques are not visible.

Results

Figure 3:
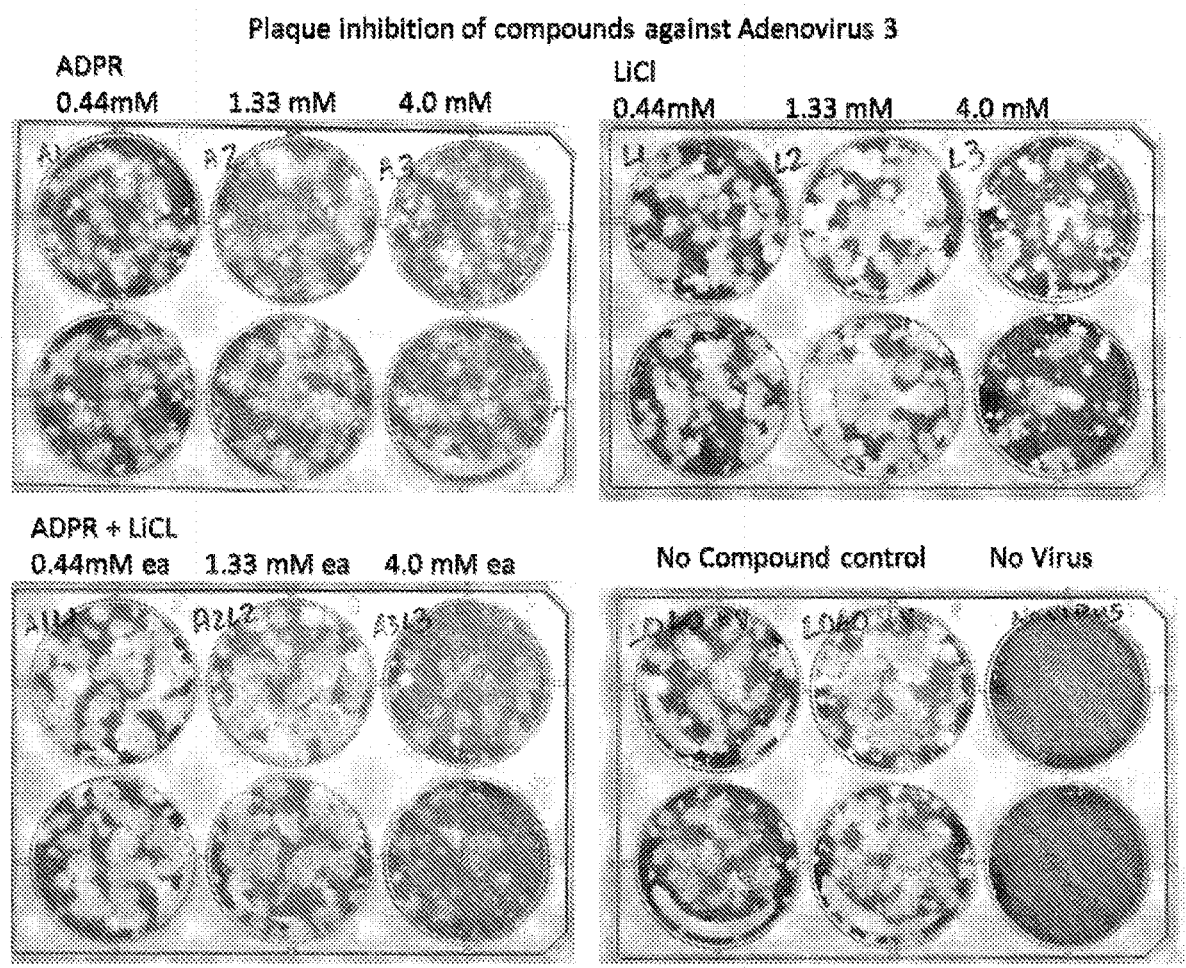
FIG. 3 depicts plaque formation from adenovirus serotype 3 in A549 cells and the effects of ADPR (monosodium salt), LiCl, and combination of ADPR (monosodium salt) and LiCl at 0.4 mM, 1.33 mM, and 4 mM concentrations.
Figure 4:
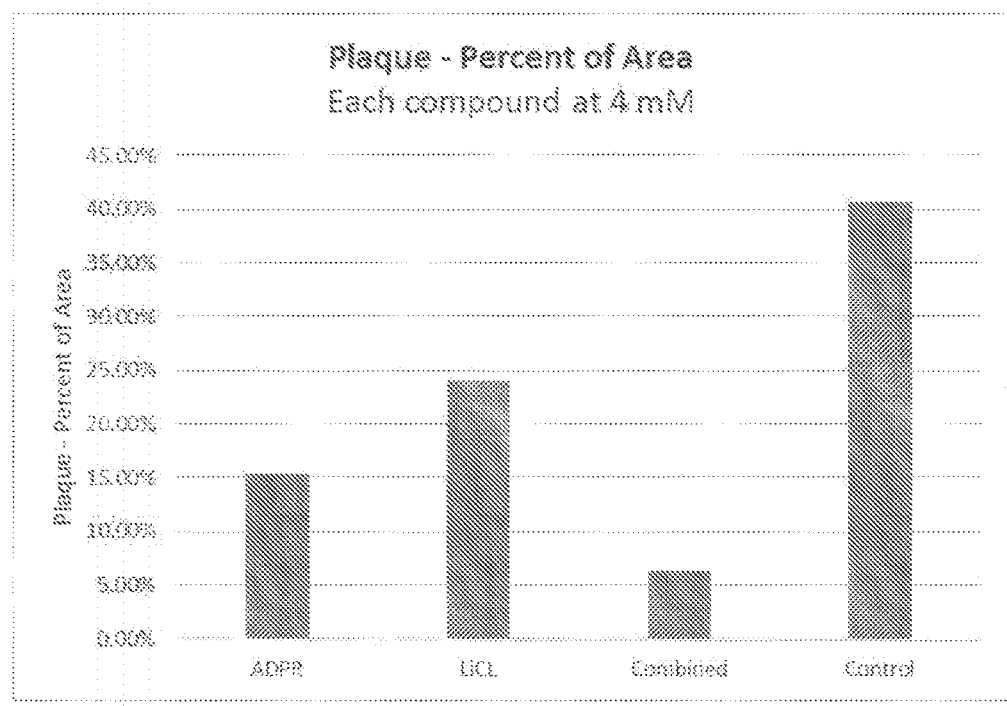
FIG. 4 is a graph of percent plaque coverage from adenovirus serotype 3 in A549 cells and the effects of ADPR (monosodium salt), LiCl, and combination of ADPR (monosodium salt) and LiCl at 4 mM concentration.

Plaque size was reduced with treatment of Sample A at 0.44, 1.33 and 4.0 mM as compared to control. Adenovirus plaques appeared much larger than the control at 1.33 mM concentration of Sample L alone. A synergistic effect of combining Sample A and Sample L at 4 mM each was observed—plaques were determined to be smaller on average than the control-treated cultures. Neither Sample was cytotoxic at concentrations tested. Plaque counts are depicted in Table 3 below, and plate images are depicted in FIG. 3. FIG. 4 depicts percent plaque inhibition of adenovirus serotype 3 by Sample A (i.e., ADPR), Sample L (i.e., LiCl), and combination of Sample A and Sample L at 4 mM concentration. This analysis was done by routine image analysis to determine percent plaque area (see FIG. 4). Image analysis was performed with Adobe Photoshop. To perform this analysis, contrast was adjusted equally across plates in order to better identify the plaque formations. A standard circular area of 45,621 pixels per plate was selected at the center of each plate to avoid edge artifacts related to the cell culture. The 'Color Range' function was then used to identify the number of white pixels within the circular area and then divided by the total pixel area to compute the percent plaque area. Results were analyzed in Microsoft Excel 2016. Values for duplicate plates were averaged. As shown in FIG. 4, a synergistic effect was observed by combining Sample A and Sample L at 4 mM concentration of each sample. The combination had a 31% improvement (observed 6.31% vs. expected 9.11%) over the expected effect if the compounds were just additive.

TABLE 3

Plaque Counts, Toxicity Scores and Plate Codes

| Group | 0 mM Sample L | 0.44 mM Sample L | 1.33 mM Sample L | 4.0 mM Sample L |
|---|---|---|---|---|
| 1  0 mM Sample A | 71, 78, 59, 79<br>T = 0<br>Plate code L0A0 | 82, 77<br>T = 0<br>Plate code L1 | 80, 84<br>very large plaques<br>T = 0<br>Plate code L2 | 66, 63<br>T = 0<br>Plate code L3 |
| 2  0.44 mM Sample A | 65, 68<br>T = 0<br>Plate code A1 | 73, 63<br>T = 0<br>Plate code A1L1 | | |
| 3  1.33 mM Sample A | 64, 57<br>T = 0<br>Plate code A2 | | 71, 71<br>T = 0<br>Plate code A2L2 | |
| 4  4.0 mM Sample A | 58, 66<br>T = 0<br>Plate code A3 | | | 53, 67<br>medium plaques<br>T = 0<br>Plate code A3L3 |
| 5  Controls | | 100 μM Cidofovir<br>0, 0 | 33 μM Cidofovir<br>45, 51<br>Pinpoint plaques | 3 μM Cidofovir<br>72, 78<br>small plaques |

This assay used the same raw materials and control drug as described in Example 1.

6.3 Example 3. Test Pilot Study to Develop a Viral Conjunctivitis Model in New Zealand White Rabbits Purpose/Objective (s): The purpose of this study was to develop a viral conjunctivitis model in New Zealand White rabbits.

Protocol

Animal Preparation: Three animals were anesthetized with an intramuscular injection of ketamine (up to 50 mg/kg) and xylazine (up to 10 mg/kg) for the viral inoculation procedures. Following anesthesia, the eyes were cleaned with betadine and then rinsed with basic salt solution (BSS). A wire lid speculum was inserted to retract the lids. One to two drops of proparacaine (0.5%) was applied to both eyes. Corneal scarification was performed on Day 0. The epithelium layer of each cornea was scarified with a 3×3 cross-hatch patter scratch with a 25 gauge sterile needle.

Following corneal scarification, both corneas of each rabbit were inoculated topically with 2×10⁶ PFU of adenovirus, serotype 5 (Ad5). To accomplish this, 0.02 mL of the 1.1×10⁸ PFU Ad5/mL solution was delivered topically using a sterile pipette. Following Ad5 inoculation, animals were recovered from the anesthetic event.

Test and Control Article

The test article, 2.0% adenosine-diphosphoribose (sodium salt) formulation containing 0.057% tetraborate, 1.20% boric acid, and 0.02% PEG-300, was prepared and its pH was adjusted to 7.08. The control article, a buffer solution containing 0.2% NaCl, 0.057% tetraborate, 1.20% boric acid, and 0.02% PEG-300, was prepared and its pH was 6.97.

Test and Control Article Administration

Treatments were given according to the study design table below (see Table 4). The test or control article was administered via topical administration three times daily (25 μL per drop with two drops per dose) (TID) for the study duration.

TABLE 4

Study Design

| Animal | Treatment (OU) | N | Clinical Ophthalmic Exams | Slit lamp Photos |
|---|---|---|---|---|
| 1 | Untreated Control | 1 | Days 1, 2, 3, 4, 7, & 10 (±1 day) | Days 1, 3, 7, & 10 (±1 day) |
| 2 | Vehicle Control - buffered solution (Topical, TID) | 1 | Days 1, 2, 3, 4, 7, & 10 (±1 day) | Days 1, 3, 7, & 10 (±1 day) |
| 3 | Test Article Dose A - 2% TA in buffered solution (Topical, TID) | 1 | Days 1, 2, 3, 4, 7, & 10 (±1 day) | Days 1, 3, 7, & 10 (±1 day) |

TID: three times a day

Summary of the Results

Ocular examinations using the McDonald-Shadduck scoring system showed some discharge above normal (scores of "1") from days 1 through 4, but was more abundant for all groups on the day 7 exams (scores of "2"). By day 10 the discharge was less except for the group 2 animal P7279. The conjunctiva congestion was not as robust, however, the day 1 scores were the highest (50% of the scores were "2") for all three animals. Although the conjunctival congestion scores for days 7 and 10 were mostly "2," the congestion was limited to the third eyelid. It should be noted that the third eyelid is even more sensitive to irritants then the conjunctiva itself.

FIGS. 5-7 summarize the changes observed on the corneal surface at the site of the viral inoculation. Corneal scratches provide the base for the virus to attach to the corneal epithelium and were the sites where the corneal opacities and cloudiness appeared. Over the course of the study, animal no. P7280 treated with the test article appeared to have the largest improvement with decreased corneal opacities both on the corneal scratches and the corneal surface areas as well.

Conclusion

The Test Article Dose A—2% appeared to reduce the corneal opacities when compared to the vehicle and the untreated control.

6.4 Example 4. Synthesis of Dilithium ADPR (Li₂ ADPR)

Dilithium ADPR (Li₂ ADPR) was synthesized from the free acid of nicotinamide adenine dinucleotide (NAD+) under lithium hydroxide hydrolysis conditions. The synthetic scheme is outlined below:

Scheme 1. Syntheis of dilithium ADPR (Li₂ADPR)

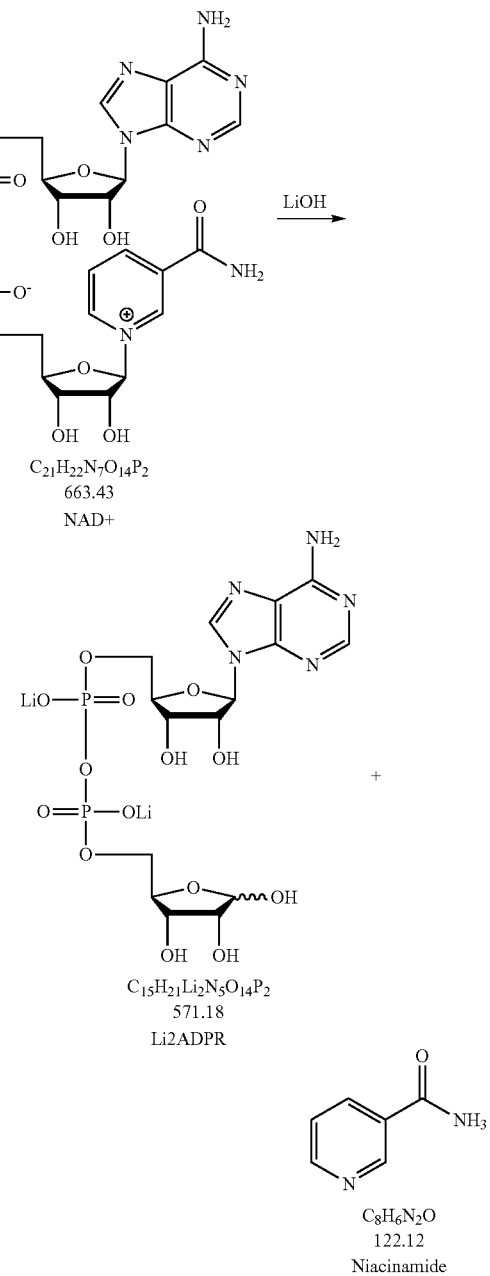

The materials utilized are shown in Table 5.

TABLE 5

Materials

| Name | Grade/Part # | Vendor | Lot # |
|---|---|---|---|
| β-Nicotinamide adenine dinucleotide (NAD+) | ACS/NAD+ | Codexis | 008101 |
| Lithium hydroxide (LiOH•H₂O) | ACS/L127 | Fisher Scientific | 884256 |
| Deionized water | NA | Testing facility | NA |

The instrumentation parameters are shown in Table 6.

TABLE 6

Instrumentation Parameters

| Pump | ThermoFinnigan Surveyor LC Pump |
|---|---|
| Detector | ThermoFinnigan Surveyor PDA Detector |
| Autosampler | ThermoFinnigan Surveyor Autosampler |
| Column | Phenomenex-Kinetex C18, 100 × 4.6 mm |
| Column Temperature | 25° C. |
| Autosampler Temperature | 25° C. |
| Injection Volume | 4-20 µL |
| Mobile phase A | 35 mM phosphate buffer at pH 6.8 |
| Flow rate | 0.75 mL/min |
| Run Time | 10.0 min |
| Detection | 254 nm as a PDA absorption wavelength |

The starting material β-nicotinamide adenine dinucleotide (NAD+) was purchased from Codexis as a free acid and was used for the hydrolysis by lithium hydroxide to remove the nicotinamide moiety, resulting in adenosine 5'-diphosphoribose (ADPR) lithium salt. Excess LiOH was added to maintain the reaction solution pH between 10-10.5. The hydrolysis was monitored by HPLC. Hydrolysis was judged to be complete after 8 days. The hydrolyzed product was isolated by trituration in MeOH, water and EtOH to remove excess LiOH and nicotinamide.

Experiment and Results

NAD+ (10.00 g, 15.07 mmol) was dissolved in water (250 L). Solid LiOH was added to adjust the solution from pH 2.78 to 11.21. The amount of LiOH—H₂O added was 0.809 g. Slight color change to light yellow was noticed and slightly exothermic process was detected. Gradual pH decrease was observed while the hydrolysis was proceeding. The solution was stirred at room temperature (RT) for 8 days, during which LiOH·H₂O was added periodically to maintain the reaction solution pH 10-10.5. The total amount of LiOH·H₂O utilized to drive the reaction to completion was 1.624 g (2.57 eq.). The progress of the reaction was monitored by HPLC analysis. At the end of the reaction, the solution had a red-wine color with small amount of white precipitate on top of the solution. The solid was removed by filtration. Activated charcoal (~35 g) was added. The mixture was stirred at RT for 20 hours and filtered to give a light yellow filtrate. The filtrate was concentrated by rotary evaporation. The residue was suspended in MeOH (100 mL), stirred at RT for 1 hr and filtered. An aliquot of the solid from the filtration was dissolved in water and its pH was 10. The filtrate was evaporated and the residual solid was dried under high vacuum. An aliquot of the solid was dissolved in water and its pH was ~7. This solid was suspended in EtOH (50 mL) and the suspension was stirred at RT for 2 days. The solid was collected by filtration, rinsed with EtOH (10 mL) and further dried under high vacuum to give 3.246 g of a light yellow solid.

This solid sample was submitted for elemental analysis and the results are shown in Table 7, confirming the product as a dilithium salt with a molecular formula $C_{15}H_{21}Li_2N_5O_{14}P_2$—$1.1H_2O$. ADPR was further confirmed by HPLC (see FIG. 8) and mass spectrometry (see FIG. 9) analysis.

TABLE 7

Elemental analysis results

| Molecular Formula | | % C | % H | % N | % P | % Li | K.F. (%) |
|---|---|---|---|---|---|---|---|
| $C_{15}H_{21}Li_2N_5O_{14}P_2$—$1.1H_2O$ | Calculated | 30.48 | 3.96 | 11.85 | 10.48 | 2.35 | 3.35 |
| | Found | 30.03 | 4.24 | 10.63 | 8.27 | 2.44 | 3.29 |

6.5 Example 5. Efficacy of Dilithium ADPR Against Adenovirus—In Vitro Study

Background

Dilithium ADPR, 150 mg powder, was stored in a glass vial ("Sample A") at 4° C. in the dark until use. On the day of assay, Sample A was solubilized to 200 mg/ml in 750 µL water for irrigation, then further diluted to target concentrations. The compound went into solution easily. Solubilized Sample A was tested for plaque inhibitory properties against Adenovirus 3 and Adenovirus 5 (Ad3 & Ad5).

Dilutions

Solubilized Sample A was diluted to 4 mg/mL, 2 mg/mL, 1 mg/mL and 0.5 mg/mL in Virus Growth Media (DMEM, 2% Fetal Bovine Serum (FBS) and antibiotic, antimycotic).

Approach

A549 cells were plated 7×10⁴ cells per well in 6-well plates. After 18 hours, growth media was removed and 1 mL of each sample mixtures was added per well. After incubating for one hour at 37° C., approximately 50-75 plaque forming units Ad3 and separately Ad5 were added per well. Virus adsorbed to the cells for two hours and then media was aspirated from the monolayers and replaced with Virus Growth Media containing Sample A dilutions of 0, 0.5, 1.0, 2.0, and 4.0 mg/mL, and agarose.

Results

Ad3 and Ad5 plaque size and number were reduced by Sample A at 4 mg/mL and 2 mg/mL. In addition, the monolayers showed moderate thinning at 4 and 2 mg/mL compared to control wells with less intense staining than control wells. The thin monolayer made it hard to delineate plaques. Very few plaques were visible as compared to control. At dilutions of 1 mg/mL and 0.5 mg/mL, Ad3 and Ad5 plaque size and number were reduced in number and size, and the monolayer showed slight thinning as compared to cell control wells. Mean plaque counts at Sample A concentrations were as follows:

Ad3: 4 mg/mL-29; 2 mg/mL-10; 1 mg/mL-44; 0.5 mg/mL-54; 0 mg/mL-55

Ad5: 4 mg/mL-7; 2 mg/mL-7; 1 mg/mL-25; 0.5 mg/mL-53; 0 mg/mL-65

Conclusion

Dilithium ADPR demonstrated that it effectively reduced cytopathic effect as indicated by plaque size and number caused by adenovirus (Ad3 and Ad5) grown in cell culture in A549 cells. In addition, the dose responsive thinning of the monolayer is consistent with the reduced replication observed in other cancer cell lines described in Example 7.

6.6 Example 6. Efficacy in Keratoconjunctivitis—In Vivo Study

This study was designed to evaluate the efficacy of the Dilithium ADPR in a viral conjunctivitis model in rabbits.

6.6.1 Experimental Design

6.6.1.1 Test System

Species: Oryctolagus cuniculus
Strain: New Zealand White rabbits
Sex: Female
Age: Commensurate with weight
Weight: Approximately 2.5 to 3.0 kilograms at study start
Number: 8 (naïve)
Method of Identification: Ear tag and cage label
Minimum Acclimation: 5 days

6.6.1.2 Housing

Animals were housed under animals biosafety level 2 (ABSL-2) conditions following Ad5 inoculation. Animals were singly housed prior to and during the study in order to decrease the likelihood of ocular injuries from cage mates.

6.6.1.3 Test/Control Articles

1. Inoculum—Adenovirus serotype 5 (Ad5)
   (a) Physicochemical Characteristics and Composition Description: Virus propagated in A549 cells in DMEM with 8% fetal bovine serum. Cells and supernatant harvested, sonicated, and clarified by low speed centrifugation. Infectious titer by TCID50: $5.0 \times 10^9$ plaque-forming-units (PFU) per mL.
   (b) Storage Condition: frozen at −60 to −80° C.
2. Test Article—Dilithium ADPR
   (a) Molecular weight: approximately 571.18
   (b) Storage Condition: Refrigerated at 2-8° C.
3. Control Vehicle
   (a) Composition: 0.31% sodium chloride, 0.1% sodium tetraborate, 1% boric acid, 0.35% polyethylene glycol 300 (PEG-300) in deionized (DI) water
   (b) Storage Condition: Refrigerated at 2° C.-8° C.
4. Test/Control Article Preparation
   (a) Ad5 was supplied in a single aliquot for both days of inoculation. Immediately prior to the first viral inoculation on Day −1, the virus was thawed and brought to room temperature. 0.05 mL (50 μL) of the $5.0 \times 10^9$ PFU Ad5/mL solution was diluted with 1.5 mL of Dulbecco's Modified Eagle Medium (DMEM) to create a $1.61 \times 10^8$ PFU Ad5/mL solution. After the first inoculation on Day −1, the remaining virus solution was stored refrigerated at 2-8° C. until the second inoculation on Day 0. Virus solution was not re-frozen.
   (b) Vehicle: 55.8 mg sodium chloride, 18 mg of sodium tetraborate, 180 mg of boric acid, and 63 mg of PEG-300 were weighed out into a vial. 14 mL DI water was added, and vial contents were swirled, vortexed, and/or sonicated if needed until a clear solution is formed. The pH of the solution was tested using pH tester strips and adjusted to 7.0-7.2, if necessary, using sodium hydroxide (NaOH) or additional boric acid. The volume was then brought up to 18 mL with additional DI water to make a 0.31% sodium chloride, 0.1% sodium tetraborate, 1% boric acid, 0.35% PEG-300 solution. The vial contents were sterile filtered through a 0.2 or 0.22 μm filter.
   (c) Dilithium ADPR—High Dose: 240 mg of dilithium ADPR was weighed out into a vial. 12 mg of sodium tetraborate, 120 mg of boric acid, and 42 mg of PEG-300 were weighed out into a separate vial. 7 mL DI water was added, and vial contents were swirled, vortexed, and/or sonicated if needed until a clear solution is formed. The solution was transferred to the vial containing dilithium ADPR. The volume was brought up to 9.5 mL with DI water, and vial contents were swirled, vortexed, and/or sonicated if needed until a clear solution is formed. The pH of the solution was tested using pH tester strips and adjusted to 7.0-7.2, if necessary, using sodium hydroxide (NaOH) or additional boric acid. The volume was then brought up to 12 mL with additional DI water to make a 2.0% dilithium ADPR solution. The vial contents were sterile filtered through a 0.2 or 0.22 μm filter.
   (d) Dilithium ADPR—Mid Dose: 1 part vehicle and 1 part high dose formulation were mixed to make a 1.0% dilithium ADPR solution.
   (e) Dilithium ADPR—Low Dose: 3 parts vehicle and 1 part high dose formulation were mixed to make a 0.5% dilithium ADPR solution.

Dosing solutions were divided into aliquots for individual dosing events (3 vials per day) and stored refrigerated at 2-8° C. Prior to dosing, dosing solutions were allowed to come to room temperature. After dosing, aliquots were stored or discarded in the room holding the study animals, and were not transferred back into the formulation room or any other room in the vivarium.

6.6.1.4 Details of Test/Control Article Administration

1. Pre-Treatment Examinations

Prior to placement on study, each animal underwent an ophthalmic examination (slitlamp biomicroscopy and indirect ophthalmoscopy) performed by the Study Director. Ocular findings were scored according to a modified McDonald-Shadduck Scoring System (see Section 6.6.1.5). The acceptance criteria for placement on study was scores of "0" for all variables.

2. Anesthesia

Animals were anesthetized with an intramuscular injection of ketamine (up to approximately 50 mg/kg) and xylazine (up to approximately 10 mg/kg) for the viral inoculation procedures.

3. Corneal Scarification and Viral Inoculation Procedure

Viral inoculation was performed in both eyes of all study animals on Days −1 and 0. Animals were anesthetized as described above. The eyes were cleaned with betadine (no betadine was used on Day 0) and then rinsed with basic salt solution (BSS). A wire lid speculum was inserted to retract the lids. One to two drops of proparacaine (0.5%) were applied to both eyes. Additional topical anesthetics may be used during the procedure as necessary. Corneal scarification was performed in both eyes by scarifying the epithelium layer of each cornea with a 3×3 cross-hatch patter scratch with a 25 gauge sterile needle. Following corneal scarification, both corneas of each rabbit were inoculated by delivering 0.015 mL (15 μL) of the $1.61 \times 10^8$ PFU Ad5/mL solution topically to each eye for each inoculation using a sterile pipette, resulting in a dose of $2.42 \times 10^6$ PFU of Ad5 per eye. Following each Ad5 inoculation, animals were recovered from the anesthetic event.

4. Group Assignment

On Day 1 prior to dosing, infection severity were evaluated in all animals, and the animals were assigned to one of 4 experimental groups (see below) based on infection severity. Animals were assigned a numeric rank from 1 to 8 according to infection severity in a decreasing order (the animal with the most severe infection was assigned rank=1). They were then assigned to the experimental groups according to the following scheme:

| Group Assignment Table | | | |
|---|---|---|---|
| Group 1 | Group 2 | Group 3 | Group 4 |
| 1 | 2 | 3 | 4 |
| 8 | 7 | 6 | 5 |

5. Test/Control Article Administration

Test/control articles were administered topically into both eyes (OU) as two 25 μL drops three times daily (to be completed within an 8-hour day; AM, mid-day, and PM dose all ~3-4 hours apart) for 7 days starting on Day 1 (~24 hours after the second virus inoculation) according to the Study Design table below:

| Group | N | Treatment (OU) | Dose | Dose Route | Dose Volume | Slit-lamp Exams |
|---|---|---|---|---|---|---|
| 1 | 2 | Vehicle Control | NA | Topical, TID*, on Days 1-7 | 2 × 25 μL/eye per dose | Days 1, 2, 3, and 7 |
| 2 | 2 | Dilithium ADPR | 0.5% | | | |
| 3 | 2 | Dilithium ADPR | 1.0% | | | |
| 4 | 2 | Dilithium ADPR | 2.0% | | | |

OU: both eyes;
NA: not applicable;
TID: three times daily
*Dosing was performed within an 8-hour day; AM, mid-day, and PM doses were all at least ~3-4 hours apart.
**Day 1 examinations and photography were performed prior to the start of dosing; all other examinations and photography were performed ~30 minutes after the third dose that day 6. In-Life Observations and Measurements (a) General Health Observations: Animals were observed within their cages once daily throughout the study period. Each animal was observed for changes in general appearance and behavior. Any abnormal observations were reported to the Study Director. General health observations were performed and recorded daily starting on Day −1 and continuing throughout the duration of the study (total of 9 days).

(b) Body Weights: Animals were weighed prior to inoculation and prior to euthanasia.

(c) Clinical Ophthalmic Examinations: Clinical ophthalmic examinations (slit-lamp biomicroscopy only) were performed on Days 1, 2, 3, and 7. On Day 1, examinations were performed prior to the start of dosing. On all other days, examinations were performed ~30 minutes following the last dose of the day (i.e., the third dose). On Day 7, examinations were performed immediately prior to euthanasia of the animals. Slit-lamp examinations were performed by the Study Director. Ocular findings were scored according to a modified McDonald-Shadduck Scoring System (see Section 6.6.1.5 below).

(d) Slit-lamp Photographs: Slit-lamp photographs were taken on Days 1, 3, and 7. On Day 1, photographs were taken prior to the start of dosing. On all other days, photographs were taken ~30 minutes following the last dose of the day (i.e., the third dose). On Day 7, photographs were taken immediately prior to euthanasia of the animals.

6.6.1.5 Modified McDonald-Shadduck Scoring System

A modified McDonald-Shadduck Scoring System is illustrated below (see, T. McDonald and J. A. Shadduck, "Eye irritation," in Advances in Modern Toxicology: Dermatoxicology, F. Marzulli and H. I. Maibach, Eds., pp. 579-582, Hemisphere Publishing Corporation, Washington, DC, USA, 1977):

1. Examination
    1.1. Use the slit lamp to observe the following:
        A. Conjunctival Discharge
        B. Conjunctival Congestion
        C. Conjunctival Swelling
        D. Cornea
        E. Surface Area of Cornea Involvement
        F. Pannus
        G. Pupillary Response
        H. Aqueous Flare
        I. Aqueous Cell
        J. Iris Involvement
        K. Lens
        L. Vitreous flare
        M. Vitreous cell
    1.2. Use the Indirect Ophthalmoscope for the following
        A. Vitreous
        B. Vitreal Hemorrhage
        C. Retinal Detachment
        D. Retinal Hemorrhage
        E. Choroidal/Retinal Inflammation
    1.3. Prepare animal for observation by using one of three solutions to dilate the pupil. Usually two drops of ophthalmic preparations of atropine, tropicamide, or phenylephrine is sufficient.

A. The choice of dilator will generally be outlined in the study protocol.
1.4. Wait until pupil of animal appears to be dilated. It may take up to 60 minutes to achieve pupil dilation.
2. Conjunctival Discharge
2.1. Discharge is defined as a whitish gray precipitate from the eye.
2.2. Scoring may be taken as follows:
A. 0=Normal. No discharge.
B. 1=Discharge above normal and present on the inner portion of the eye but not on the lids or hairs of the eyelids.
C. 2=Discharge is abundant, easily observed and has collected on the lids and hairs of the eyelids.
D. 3=Discharge has been flowing over the eyelids so as to wet the hairs substantially on the skin around the eye.
3. Conjunctival Congestion
3.1. Congestion causes the blood vessels of the eye to become enlarged.
3.2. Scoring may be taken as follows:
A. 0=Normal. May appear blanched to reddish pink without perilimbal injection (except at the 12:00 and 6:00 positions) with vessels of the palpebral and bulbar conjunctiva easily observed.
B. 1=A flushed, reddish color predominantly confined to the palpebral conjunctiva with some perilimbal injection but primarily confined to the lower and upper parts of the eye from the 4:00 to 7:00 and 11:00 to 1:00 positions.
C. 2=Bright red color of the palpebral conjunctiva with accompanying perilimbal injection covering at least 75% of the circumference of the perilimbal region.
D. 3=Dark, beefy red color with congestion of both the bulbar and palpebral conjunctiva along with pronounced perilimbal injection and the presence of petechia on the conjunctiva. The petechia generally predominates along the nictitating membrane and upper palpebral conjunctiva.
4. Conjunctival Swelling
4.1. Definition: Swelling of the conjunctiva.
4.2. Scoring may be taken as follows:
A. 0=Normal or no swelling of the conjunctival tissue
B. 1=Swelling above normal without eversion of the eyelids (easily discerned by noting upper and lower eyelids are positioned as in the normal eye); swelling generally starts in the lower cul-de-sac near the inner canthus.
C. 2=Swelling with misalignment of the normal approximation of the lower and upper eyelids; primarily confined to the upper eyelid so that in the initial stages, the misapproximation of the eyelids begins by partial eversion of the upper eyelid. In this stage the swelling is confined generally to the upper eyelid with some swelling in the lower cul-de-sac.
D. 3=Swelling definite with partial eversion of the upper and lower eyelids essentially equivalent. This can be easily observed by looking at the animal head-on and noting the position of the eyelids; if the eye margins do not meet, eversion has occurred.
E. 4=Eversion of the upper eyelid is pronounced with less pronounced eversion of the lower eyelid. It is difficult to retract the lids and observe the perilimbal region.

5. Iris Involvement
5.1. Check the iris for hyperemia of the blood vessels.
5.2. Scoring may be taken as follows:
A. 0=Normal iris without any hyperemia of the blood vessels.
B. 1=Minimal injection of the secondary vessels but not tertiary vessels. Generally uniform but may be of greater intensity at the 12:00 to 1:00 or 6:00 position. If confined to this area, the tertiary vessels must be substantially hyperemic.
C. 2=Minimal injection of tertiary vessels and minimal to moderate injection of the secondary vessels.
D. 3=Moderate injection of the secondary and tertiary vessels with slight swelling of the iris stroma (the iris surface appears slightly rugose, usually most predominant near the 3:00 and 9:00 positions).
E. 4=Marked injection of the secondary and tertiary vessels with marked swelling of the iris stroma. The iris appears rugose; may be accompanied by hemorrhage (hyphema) in the anterior chamber.
6. Cornea
6.1. Check the Cornea for any abnormalities.
6.2. Scoring may be taken as follows:
A. 0=Normal Cornea
B. 1=Some loss of transparency. Only the epithelium and/or the anterior half of the stroma are involved. The underlying structures are clearly visible although some cloudiness may be readily apparent.
C. 2=Involvement of the entire thickness of the stroma. With diffuse illumination, the underlying structures are just barely visible (can still observe flare, iris, pupil response, and lens).
D. 3=Involvement of the entire thickness of the stroma. With diffuse illumination, the underlying structures cannot be seen.
7. Surface Area of Cornea Involvement
7.1. Check the eye for cloudiness in the stromal region.
7.2. Scoring may be taken as follows:
A. 0=Normal
B. 1=1-25% area of stromal cloudiness.
C. 2=26-50% area of stromal cloudiness.
D. 3=51-75% area of stromal cloudiness.
E. 4=76%-100% area of stromal cloudiness.
8. Pannus
8.1. Check for vascularization of Cornea
8.2. Scoring may be taken as follows:
A. 0=No pannus (vascularization of the cornea)
B. 1=Vascularization present but vessels have not invaded the entire cornea circumference.
C. 2=Vessels have invaded 2 mm or more around entire corneal surface.
9. Pupillary Response
9.1. Check for any blockage or a sluggish response in the pupillary region.
9.2. Scoring may be taken as follows:
A. 0=Normal pupil response.
B. 1=Sluggish or incomplete pupil response.
C. 2=No pupil response.
D. 3=No pupil response due to pharmacological blockage.
10. Aqueous Flare
10.1. Breakdown of the blood-aqueous barrier.
10.2. Field size is a 1 mm×1 mm slit beam.
10.3. Scoring may be taken as follows (based on Jabs DA et al., 2005):
A. 0=None
B. 1=Faint C. 2=Moderate (iris and lens details clear)
D. 3=Marked (iris and lens details hazy)
E. 4=Intense (fibrin or plastic aqueous)
11. Vitreous Flare
    11.1. Opacity or fogginess of the vitreous humor.
    11.2. Scoring may be taken as follows (based on Opremcak EM, 2012):
        A. 0=None (nerve fiber layer [NFL] clearly visible)
        B. 1=Faint (optic nerve and vessels clear, NFL hazy)
        C. 2=Moderate (optic nerve and vessels hazy)
        D. 3=Marked (optic nerve only visible)
        E. 4=Intense (no optic nerve visible)
12. Aqueous Cell
    12.1. Cellular observation in the aqueous humor.
    12.2. Field size is a 1 mm×1 mm slit beam.
    12.3. Scoring may be taken as follows (based on Jabs DA et al., 2005):
        A. 0=None
        B. 0.5=Trace (1-5)
        C. 1=6-15
        D. 2=16-25
        E. 3=26-50
        F. 4=>50
13. Vitreous Cell
    13.1. Cellular observation in the vitreous humor.
    13.2. Scoring may be taken as follows (based on Opremcak EM, 2012):
        A. 0=Trace (0-10)
        B. 1=11-20
        C. 2=21-30
        D. 3=31-100
        E. 4=>100
14. Lens
    14.1. Observe the lens for any cataracts.
    14.2. Scoring may be taken as follows:
        A. 0=Lens clear.
        B. 1=Anterior (cortical/capsular).
        C. 2=Nuclear.
        D. 3=Posterior (cortical/optical).
        E. 4=Equatorial.
15. Vitreous
    15.1. Observe the vitreous for any abnormalities.
    15.2. Scoring may be taken as follows:
        A. 0=Clear vitreous.
        B. 1=Few scattered opacities, fundus unimpaired.
        C. 2=Moderate scattered opacities, fundus details somewhat obscured.
        D. 3=Many opacities, marked blurring of fundus details.
        E. 4=Dense opacities, no fundus view
16. Vitreal Hemorrhage
    16.1. Observe the vitreous for any hemorrhage.
    16.2. Scoring may be taken as follows:
        A. 0=None
        B. 1=1-25%
        C. 2=26-50%
        D. 3=51-75%
        E. 4=76-100%
17. Retinal Detachment
    17.1. During a retinal detachment, bleeding from small retinal blood vessels may cloud the interior of the eye, which is normally filled with vitreous fluid.
    17.2. Scoring may be taken as follows:
        A. 0=None
        B. 1=Rhegmatogenous (retinal detachment occurs when subretinal fluid accumulates in the potential space between the neurosensory retina and the underlying retinal pigment epithelium).
        C. 2=Exudative (occurs due to inflammation, injury, or vascular abnormalities that results in fluid accumulating underneath the retina without the presence of a hole, tear, or break).
        D. 3=Tractional (occurs when fibrous or fibrovascular tissue, caused by an injury, inflammation, or neovascularization that pulls the sensory retina from the retinal pigment epithelium).
18. Retinal Hemorrhage
    18.1. Abnormal bleeding of the blood vessels in the retina.
    18.2. Scoring may be taken as follows:
        A. 0=None
        B. 1=1-25%
        C. 2=26-50%
        D. 3=51-75%
        E. 4=76-100%
19. Choroidal/Retinal Inflammation
    19.1. Inflammation of the retina and/or choroid.
    19.2 Scoring may be taken as follows:
        A. 0=None
        B. 1=Mild
        C. 2=Moderate
        D. 3=Severe

6.6.1.6 Results

The combined injury and infection with corneal scarification and Ad5 inoculation was very successful at inducing consistent corneal and conjunctival inflammation. The composite score significantly improved (p<0.01) in all of the treated groups on Days 3 and 7 compared to the baseline score on Day 1. These results are graphically shown in FIG. 10.

Furthermore, the subscores of Conjunctival Congestion and Surface Area of Corneal Involvement were primarily effected. These also showed improvement that was statistically significant in all treated groups (p<0.01 for Conjunctival Congestion and p<0.05 for Surface Area of Corneal Involvement) on Days 3 and 7 compared the baseline score on Day 1. The results are graphically shown in FIGS. 11A and 11B.

6.6.1.7 Conclusion

The results demonstrated a rapid resolution of the combined adenoviral and physical injury effects in the eyes treated with dilithium ADPR in solution. All doses used (0.5%, 1.0%, and 2.0%) were effective, p<0.01, with >80% reduction in the composite score by Day 7. The vehicle control group did not show a significant improvement by Day 7.

6.7 Example 7. Efficacy in Cancer—Cell Viability Assay (in vitro study)

Cell viability was measured by the CellTiter-Glo® cell viability assay Promega (Madison, Wis.). The CellTiter-Glo® Luminescent Cell Viability Assay is a homogeneous method to determine the number of viable cells in culture based on quantitation of the ATP present, which signals the presence of metabolically active cells. Following treatment, CellTiter-Glog was added to treatment wells and incubated at 37° C. Luminescence values were measured at using a Molecular Devices Spectramax microplate reader.

Cells were grown to 70% confluency, trypsinized, counted, and seeded in 384 well flat-bottom plates at a final concentration of 1.0'10³-1.5×10³ cells/well (Day 0). Cells were allowed to incubate in growth media for 24 hours to allow for maximum adhesion. Treatment with the test agents began on Day 1 and continued for 72 hours. At the 72-hour time point, treatment-containing media was removed. Viable cell numbers were quantified by the CellTiter-Glog cell viability assay as described above. Experiments were run with triplicate concentrations to determine growth inhibitory activity. Results from these studies were used to calculate an $IC_{50}$ value (concentration of drug that inhibits cell growth by 50 percent of control) for each compound.

Data Collection—For single agent and combination studies, data from each experiment was collected and expressed as % Cell Growth using the following calculation:

(i) % Cell Growth=$(f_{test}/f_{vehicle}) \times 100$ (ii) Where $f_{test}$ is the luminescence of the tested sample, and fvehicte is the luminescence of the vehicle in which the drug is dissolved. Dose response graphs and $IC_{50}$ values were generated using Prism 6 software (Graph-Pad).

The following compounds (concentrations) were evaluated:

(i) Lithium Chloride (30, 300, 1000, 3000 μM, and 6000 μM; 6000 μM only tested for MV411 cells)
(ii) Dilithium ADPR (30, 300, 1000, and 3000 μM)
(iii) SN38 as positive control (0.03, 0.1, 0.3, 1.0, 3.0, 10, and 30 μM)

The following cell lines were evaluated:
(i) AsPC1—human pancreatic adenocarcinoma
(ii) H1437—human, lung adenocarcinoma, non-small cell lung cancer
(iii) U87-MG—human, brain glioblastoma
(iv) MV411—human, myelomonocytic leukemia Results are expressed as $IC_{50}$ s (μM, average of two values) in the table below:

|  | Cell Type | | | |
| --- | --- | --- | --- | --- |
| Compound | AsPC1 | H1437 | U87-MG | MV411 |
| Dilithium ADPR | 569.7 | 530.9 | 1560.2 | 323.0 |
| LiCl | >3000 | >3000 | >3000 | >6000 |
| SN38 | 1.5 | 0.2 | 1.2 | 1.17 |

Conclusion: The inhibition of cellular replication by dilithium ADPR is remarkable since the lithium ion as lithium chloride at similar molar concentrations dilithium ADPR was not effective, and ADPR alone is not known to reduce cellular replication. This indicates that the two components, lithium and ADPR, combine in a synergistic fashion to stabilize these cancer cell lines and limit their replication.

6.8 Example 8. ADPR Alone (as Sodium Salt) does not Reduce Replication and/or Induce Cytotoxicity of A549 Cells ADPR, sodium Salt, (Sigma A0752), was tested in A549 (human alveolar adenocarcinoma) cell culture to determine its effect on replication. ADPR was evaluated at five concentrations by incubation for 48 hours with A549 cells (previously grown to a monolayer) at 37° C. After incubation, MTT (3-(4,5-dimethylthiaz ol-2-yl)-2,5-diphenyltetrazolium bromide) dye was added to each well and live cells were measured by blue dye incorporation.

Concentrations of ADPR (sodium salt) tested were 24, 12, 6, 3, 1.5, and 0 mg/mL. Average MTT incorporation as measured by OD560 were 0.55±0.02, 0.69±0.01, 0.72±0.04, 0.61±0.09, 0.62±0.08, and 0.67±0.02 respectively.

ADPR (sodium salt) did not reduce MTT incorporation up to 12 mg/mL, with only a mild reduction at 24 mg/mL. Therefore, ADPR alone (as the sodium salt) does not reduce cellular replication in A549 cells up to 12 mg/mL (equal to 21 mM), with only a small reduction at 24 mg/mL (eaual to 42 mM). Therefore, this further supports that the combination of lithium and ADPR as dilithium ADPR (as shown in Examples 6 and 7) demonstrates remarkable synergy between lithium and ADPR.

The invention claimed is:

1. A method for treating an adenovirus-related disease or condition in a patient, said method comprising administering to the patient an effective amount of 5'-adenosine diphosphate ribose (ADPR), or a pharmaceutically acceptable salt, solvate, hydrate, tautomer, stereoisomer, isotopologue, or polymorph thereof; wherein the patient is having or at risk of developing the adenovirus-related disease or condition; and wherein the adenovirus-related disease or condition is a disease or condition that affects any portion of the eye, ear, mouth, upper respiratory tract, or lower respiratory tract.

2. The method of claim 1, wherein the adenovirus-related disease or condition is epi-bulbar disease, conjunctivitis, keratitis, kerato-conjunctivitis, corneal abrasion, ulcerative infectious keratitis, epithelial keratitis, stromal keratitis, uveitis, acute glaucoma, blepharitis, otitis media, otitis externa, gingivitis, mucositis, pharyngitis, tonsillitis, rhinitis, sinusitis, laryngitis, croup, tracheitis, bronchitis, bronchiolitis, bronchiolar pneumonia, pneumonia, exacerbation of asthma, exacerbation of chronic obstructive pulmonary disease, or exacerbation of emphysema.

3. The method of claim 2, wherein the adenovirus-related disease or condition is keratitis, conjunctivitis, or kerato-conjunctivitis.

4. The method of claim 1, wherein the administering is done by topical, oral, parenteral, mucosal, or inhalation route of administration.

5. The method of claim 1, wherein the ADPR or a pharmaceutically acceptable salt, solvate, hydrate, tautomer, stereoisomer, isotopologue, or polymorph thereof is in a pharmaceutical composition that is in the form of a solution, suspension, emulsion, microemulsion, nanoemulsion, syrup, elixir, dry powder aerosol, liquid aerosol, tablet, or dissolving media.

6. The method of claim 5, wherein the pharmaceutical composition is in the form of a solution.

7. The method of claim 5, wherein the administering is in combination with another medicament.

8. The method of claim 7, wherein the other medicament is an antiviral compound.

9. The method of claim 7, wherein the other medicament is a metal salt.

10. The method of claim 9, wherein the other medicament is lithium chloride.

11. The method of claim 1, wherein the ADPR is in the form of its sodium salt.

12. The method of claim 1, wherein the ADPR is in the form of its lithium salt.

13. The method of claim 1, wherein the ADPR is in the form of its dilithium salt.

14. A method for treating an eye disorder or a disease or condition caused by infection, inflammation, or physical, chemical, thermal, or radiation injury in a patient, said method comprising administering to the patient an effective amount of dilithium ADPR, or a solvate, hydrate, tautomer, stereoisomer, isotopologue, or polymorph thereof; wherein the patient is having or at risk of developing the eye disorder or the disease or condition caused by infection, inflammation, or physical, chemical, thermal, or radiation injury.

15. The method of claim 14, wherein the administering is done by topical, oral, parenteral, mucosal, or inhalation route of administration.

16. The method of claim 14, wherein the administering is done by topical administration.

17. The method of claim 14, wherein the dilithium ADPR, or a solvate, hydrate, tautomer, stereoisomer, isotopologue, or polymorph thereof is in a pharmaceutical composition that is in the form of a solution, suspension, emulsion, microemulsion, nanoemulsion, syrup, elixir, dry powder aerosol, liquid aerosol, tablet, or dissolving media.

18. The method of claim 17, wherein the pharmaceutical composition is in the form of a solution.

19. The method of claim 18, wherein the pharmaceutical composition comprises dilithium ADPR and wherein the amount of dilithium ADPR in the pharmaceutical composition is in the range of about 0.1% w/w to about 1% w/w of the pharmaceutical composition.

20. The method of claim 19, wherein the pharmaceutical composition is administered by topical route of administration to the patient once a day, twice a day, or three times a day.

* * * * *